(12) United States Patent
Smith et al.

(10) Patent No.: US 8,209,006 B2
(45) Date of Patent: Jun. 26, 2012

(54) CONSTANT CURRENT ELECTROPORATION DEVICE AND METHODS OF USE

(75) Inventors: Louis C. Smith, Houston, TX (US); Ruxandra Draghia-Akli, Houston, TX (US); Amir S. Khan, Houston, TX (US); Robert H. Carpenter, Bastrop, TX (US); Jeff Darnell, The Woodlands, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 867 days.

(21) Appl. No.: 10/657,725

(22) Filed: Sep. 8, 2003

(65) Prior Publication Data

US 2005/0052630 A1    Mar. 10, 2005

Related U.S. Application Data

(63) Continuation-in-part of application No. 10/360,768, filed on Mar. 7, 2002, now Pat. No. 7,245,963.

(51) Int. Cl.
*A61N 1/30* (2006.01)
(52) U.S. Cl. ............................... 604/21; 604/20
(58) Field of Classification Search .............. 604/20–21, 604/501; 204/604, 450; 607/2, 3, 72–76, 607/115–116, 120; 435/173.5–173.7; 427/450, 427/455
See application file for complete search history.

(56) References Cited

U.S. PATENT DOCUMENTS

| | | |
|---|---|---|
| 578,611 A | 3/1897 | Rively |
| 2,223,447 A | 12/1940 | Hathaway |
| 2,239,432 A | 4/1941 | Stratton |
| 2,827,851 A | 3/1958 | Ferrara |
| 2,970,545 A | 2/1961 | Howe |
| 3,060,923 A | 10/1962 | Reiner |
| 3,078,850 A | 2/1963 | Schein et al. |
| 3,087,486 A | 4/1963 | Kilpatrick |
| 3,162,592 A | 12/1964 | Pohl |
| 3,224,436 A | 12/1965 | Massena |
| 3,313,293 A | 4/1967 | Chesebrough et al. |
| 3,568,660 A | 3/1971 | Crites et al. |
| 3,682,162 A | 8/1972 | Colyer |
| 3,834,392 A | 9/1974 | Lampman et al. |
| 3,900,020 A | 8/1975 | Lock |
| 4,016,886 A | 4/1977 | Doss et al. |

(Continued)

FOREIGN PATENT DOCUMENTS

EP    1142606    10/2001

(Continued)

OTHER PUBLICATIONS

U.S. Appl. No. 10/360,768, filed Mar. 7, 2002, Westersten et al.

(Continued)

*Primary Examiner* — Laura Bouchelle
(74) *Attorney, Agent, or Firm* — Thomas Kim

(57) ABSTRACT

An electroporation device which may be used to effectively facilitate the introduction of a macromolecule into cells of a selected tissue in a body or plant. The electroporation device comprises an electro-kinetic device ("EKD") whose operation is specified by software or firmware. The EKD produces a series of programmable constant-current pulse patterns between electrodes in an array based on user control and input of the pulse parameters and allows the storage and acquisition of current waveform data. The electroporation device also comprises a replaceable electrode disk having an array of needle electrodes, a central injection channel for an injection needle, and a removable guide disk.

21 Claims, 30 Drawing Sheets

U.S. PATENT DOCUMENTS

| | | | | |
|---|---|---|---|---|
| 4,141,359 | A * | 2/1979 | Jacobsen et al. | 604/20 |
| 4,155,363 | A | 5/1979 | Letchworth et al. | |
| 4,237,896 | A | 12/1980 | Lines | |
| 4,262,672 | A | 4/1981 | Keif | |
| 4,476,004 | A | 10/1984 | Pohl | |
| 4,524,770 | A | 6/1985 | Orandi | |
| RE32,057 | E | 12/1985 | LeVeen | |
| 4,663,292 | A | 5/1987 | Wong et al. | |
| 4,786,505 | A | 11/1988 | Lovgren et al. | |
| 4,822,470 | A | 4/1989 | Chang | |
| 4,850,956 | A | 7/1989 | Bontemps | |
| 4,969,468 | A | 11/1990 | Byers et al. | |
| 4,970,154 | A | 11/1990 | Chang | |
| 5,019,034 | A | 5/1991 | Weaver et al. | |
| 5,137,817 | A | 8/1992 | Busta et al. | |
| 5,273,525 | A | 12/1993 | Hofmann | |
| 5,318,514 | A * | 6/1994 | Hofmann | 604/20 |
| 5,389,069 | A | 2/1995 | Weaver | |
| 5,439,440 | A | 8/1995 | Hofmann | |
| 5,462,520 | A | 10/1995 | Hofmann | |
| 5,464,386 | A | 11/1995 | Hofmann | |
| 5,468,223 | A | 11/1995 | Mir | |
| 5,501,662 | A | 3/1996 | Hofmann | |
| 5,507,724 | A | 4/1996 | Hofmann et al. | |
| 5,545,130 | A | 8/1996 | Hofmann et al. | |
| 5,580,859 | A | 12/1996 | Felgner et al. | |
| 5,628,728 | A | 5/1997 | Tachibana et al. | |
| 5,674,267 | A | 10/1997 | Mir et al. | |
| 5,676,646 | A | 10/1997 | Hofmann et al. | |
| 5,688,233 | A | 11/1997 | Hofmann et al. | |
| 5,702,359 | A * | 12/1997 | Hofmann et al. | 604/20 |
| 5,704,908 | A | 1/1998 | Hofmann et al. | |
| 5,727,808 | A | 3/1998 | Broughton | |
| 5,810,762 | A | 9/1998 | Hofmann | |
| 5,859,327 | A | 1/1999 | Dev et al. | |
| 5,869,326 | A | 2/1999 | Hofmann | |
| 5,873,849 | A | 2/1999 | Bernard | |
| 5,944,710 | A | 8/1999 | Dev et al. | |
| 5,968,006 | A | 10/1999 | Hofmann | |
| 6,006,130 | A | 12/1999 | Higo et al. | |
| 6,068,650 | A | 5/2000 | Hofmann et al. | |
| 6,096,020 | A | 8/2000 | Hofmann et al. | |
| 6,110,161 | A | 8/2000 | Mathiesen et al. | |
| 6,120,493 | A | 9/2000 | Hofmann et al. | |
| 6,150,148 | A | 11/2000 | Nanda et al. | |
| 6,181,964 | B1 | 1/2001 | Hofmann et al. | |
| 6,192,270 | B1 | 2/2001 | Hofmann et al. | |
| 6,208,893 | B1 | 3/2001 | Hofmann et al. | |
| 6,216,034 | B1 | 4/2001 | Hofmann et al. | |
| 6,233,482 | B1 | 5/2001 | Gurvinder et al. | |
| 6,241,701 | B1 | 6/2001 | Hofmann et al. | |
| 6,259,946 | B1 | 7/2001 | Higo et al. | |
| 6,278,895 | B1 | 8/2001 | Bernard | |
| 6,300,108 | B1 | 10/2001 | Rubinsky et al. | |
| 6,302,874 | B1 | 10/2001 | Zhang et al. | |
| 6,314,316 | B1 | 11/2001 | Gilbert et al. | |
| 6,387,671 | B1 * | 5/2002 | Rubinsky et al. | 435/173.7 |
| 6,451,002 | B1 * | 9/2002 | Dev et al. | 604/500 |
| 7,245,963 | B2 * | 7/2007 | Draghia-Akli et al. | 604/20 |
| 2002/0010415 | A1 * | 1/2002 | Simon | 604/20 |
| 2002/0025578 | A1 | 2/2002 | MacLaughlin et al. | |
| 2002/0038112 | A1 | 3/2002 | Mathiesen et al. | |
| 2002/0198485 | A1 | 12/2002 | Dev et al. | |

FOREIGN PATENT DOCUMENTS

| | | |
|---|---|---|
| EP | 1240917 | 9/2002 |
| WO | WO 00/45823 | 8/2000 |
| WO | WO 01/89455 | 11/2001 |
| WO | WO 03/086534 A1 | 10/2003 |

OTHER PUBLICATIONS

Canatella, P. J. and M. R. Prausnitz. 2001. Prediction and Optimization of Gene Transfection and Drug Delivery by Electroporation. Gene Ther. 8:1464-9.

Dean, D. A., D. Machado-Aranda, K. Blair-Parks, A. V. Yeldandi, and J. L. Young. 2003. Electroporation as a method for high-level nonviral gene transfer to the lung. Gene Ther. 10:1608-1615.

Draghia-Akli, R., K. K. Cummings, A. S. Khan, P. A. Brown, and R. H. Carpenter. 2003a. Effects of plasmid-mediated growth hormone releasing hormone supplementation in young healthy Beagle dogs. Journal of Animal Science 81:2301-2310.

Draghia-Akli, R., K. M. Ellis, L. A. Hill, P. B. Malone, and M. L. Fiorotto. 2003b. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., A. S. Khan, K. K. Cummings, D. Parghi, R. H. Carpenter, and P. A. Brown. 2002. Electrical Enhancement of Formulated Plasmid Delivery in Animals. Technology in Cancer Research & Treatment 1:365-371.

Fattori, E., N. La Monica, G. Ciliberto, and C. Toniatti. 2002. Electro-gene-transfer: a new approach for muscle gene delivery. Somat. Cell Mol. Genet. 27:75-83.

Lee, R. C., D. Zhang, and J. Hannig. 2000. Biophysical injury mechanisms in electrical shock trauma. Annu. Rev. Biomed. Eng 2:477-509.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Martin, G. T., U. F. Pliquett, and J. C. Weaver. 2002. Theoretical analysis of localized heating in human skin subjected to high voltage pulses. Bioelectrochemistry. 57:55-64.

McMahon, J.M., E. Signori, K.E. Wells, V.M. Fazio, and D.J. Wells. 2001. Optimization of Electrotransfer of Plasmid into Skeletal Muscle by Pretreatment with Hyaluronidase—Increased Expression with Reduced Muscle Damage. Gene Ther. 8:1264-70.

Mir, L. M., M. F. Bureau, J. Gehl, R. Rangara, D. Rouy, J. M. Caillaud, P. Delaere, D. Branellec, B. Schwartz, and D. Scherman. 1999. High-efficiency gene transfer into skeletal muscle mediated by electric pulses. Proc. Natl. Acad. Sci. U. S. A 96:4262-4267.

Mir, L. M., M. F. Bureau, R. Rangara, B. Schwartz, and D. Scherman. 1998. Long-term, high level in vivo gene expression after electric pulse- mediated gene transfer into skeletal muscle. C. R. Acad. Sci. III 321:893-899.

Mor, G. and M. Eliza. 2001. Plasmid DNA vaccines. Immunology, tolerance, and autoimmunity. Mol. Biotechnol. 19:245-250.

Pilaro, A. M. and M. A. Serabian. 1999. Preclinical development strategies for novel gene therapeutic products. Toxicol. Pathol. 27:4-7.

Pliquett, U. F.; G. T. Martin, and J. C. Weaver. 2002. Kinetics of the temperature rise within human stratum corneum during electroporation and pulsed high-voltage iontophoresis. Bioelectrochemistry. 57:65-72.

Stoll, S. M. and M. P. Calos. 2002. Extrachromosomal plasmid vectors for gene therapy. Curr. Opin. Mol. Ther. 4:299-305.

* cited by examiner

20

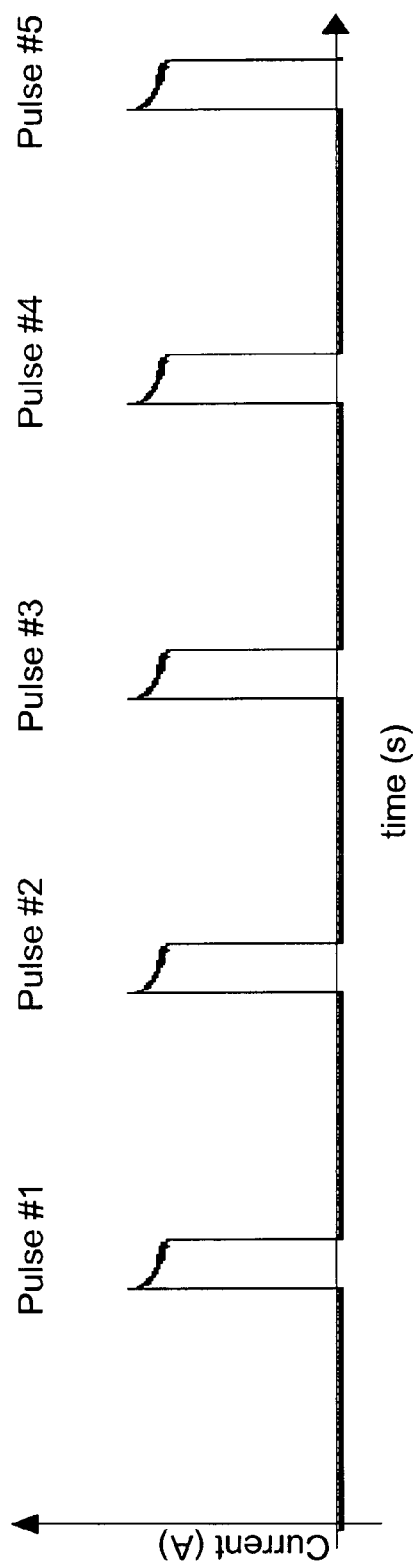
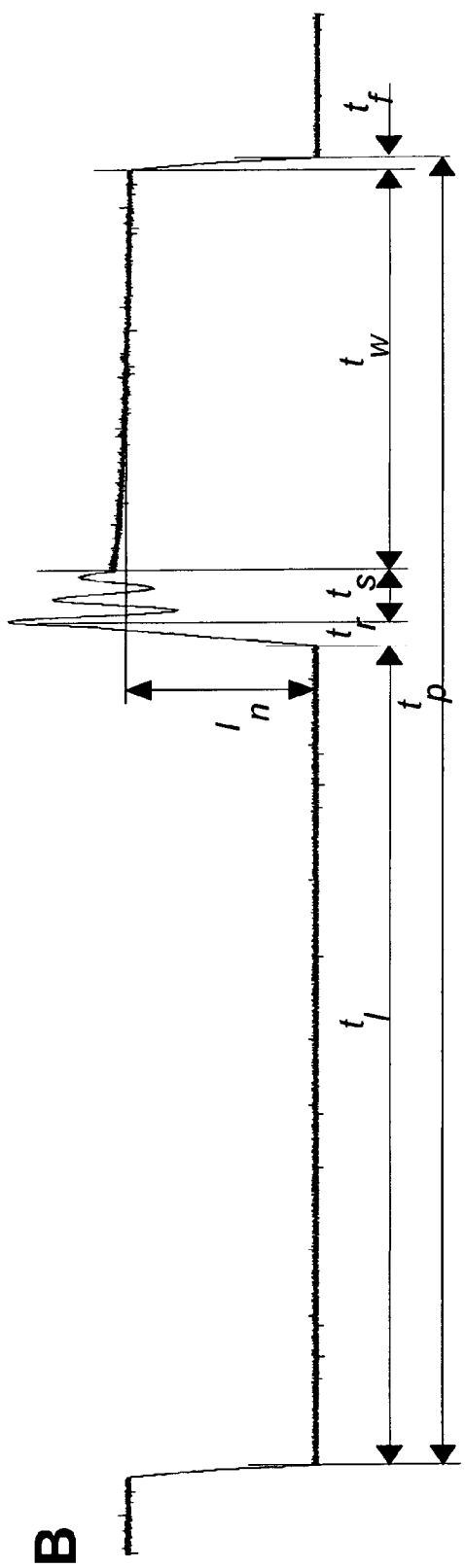
Figure 9

Figure 21

| Filename: | 00001138_03_08_13_1 6_16_02.csv | | | | |
|---|---|---|---|---|---|
| Animal Number: | 1138 | | | | |
| Pulse In Sequence: | 1 | 2 | 3 | 4 | 5 |
| Pre-wait (s): | 80 | 1 | 1 | 1 | 1 |
| Pulse Width (ms): | 52 | 52 | 52 | 52 | 52 |
| Pulse Current (A): | 0.5 | 0.5 | 0.5 | 0.5 | 0.5 |

Figure 22

| | | | | | |
|---|---|---|---|---|---|
| Electrode 1: | POS | OFF | NEG | NEG | OFF |
| Electrode 2: | OFF | POS | OFF | NEG | NEG |
| Electrode 3: | NEG | OFF | POS | OFF | NEG |
| Electrode 4: | NEG | NEG | OFF | POS | OFF |
| Electrode 5: | OFF | NEG | NEG | OFF | POS |

Figure 23

| Pulse 1 | | Pulse 2 | | Pulse 3 | | Pulse 4 | | Pulse 5 | |
|---|---|---|---|---|---|---|---|---|---|
| Voltage | Current | Voltage | Current | Voltage | Current | Voltage | Current | Voltage | Current |
| 2.34 | 0 | 2.3 | 0 | 2.34 | 0 | 2.3 | 0 | 2.34 | 0 |
| 2.39 | 0 | 2.34 | 0 | 2.39 | 0 | 2.34 | 0 | 2.34 | 0 |
| 2.3 | 0.49 | 68.25 | 0.51 | 2.34 | 0.5 | 54.47 | 0.5 | 62.09 | 0.5 |
| 69.08 | 0.49 | 66.73 | 0.51 | 55.98 | 0.5 | 53.79 | 0.5 | 58.28 | 0.5 |
| 69.03 | 0.5 | 66.24 | 0.51 | 55.5 | 0.51 | 53.25 | 0.51 | 57.89 | 0.48 |
| 69.61 | 0.51 | 66.78 | 0.5 | 55.4 | 0.49 | 53.49 | 0.51 | 57.3 | 0.5 |
| 69.81 | 0.5 | 67.12 | 0.49 | 55.3 | 0.51 | 53.44 | 0.51 | 57.3 | 0.5 |
| 70 | 0.5 | 67.42 | 0.51 | 55.25 | 0.5 | 53.54 | 0.5 | 57.5 | 0.5 |
| 70.84 | 0.5 | 66.93 | 0.49 | 54.81 | 0.52 | 53.83 | 0.49 | 57.89 | 0.51 |
| 71.28 | 0.48 | 67.76 | 0.51 | 54.96 | 0.49 | 54.57 | 0.49 | 57.79 | 0.49 |

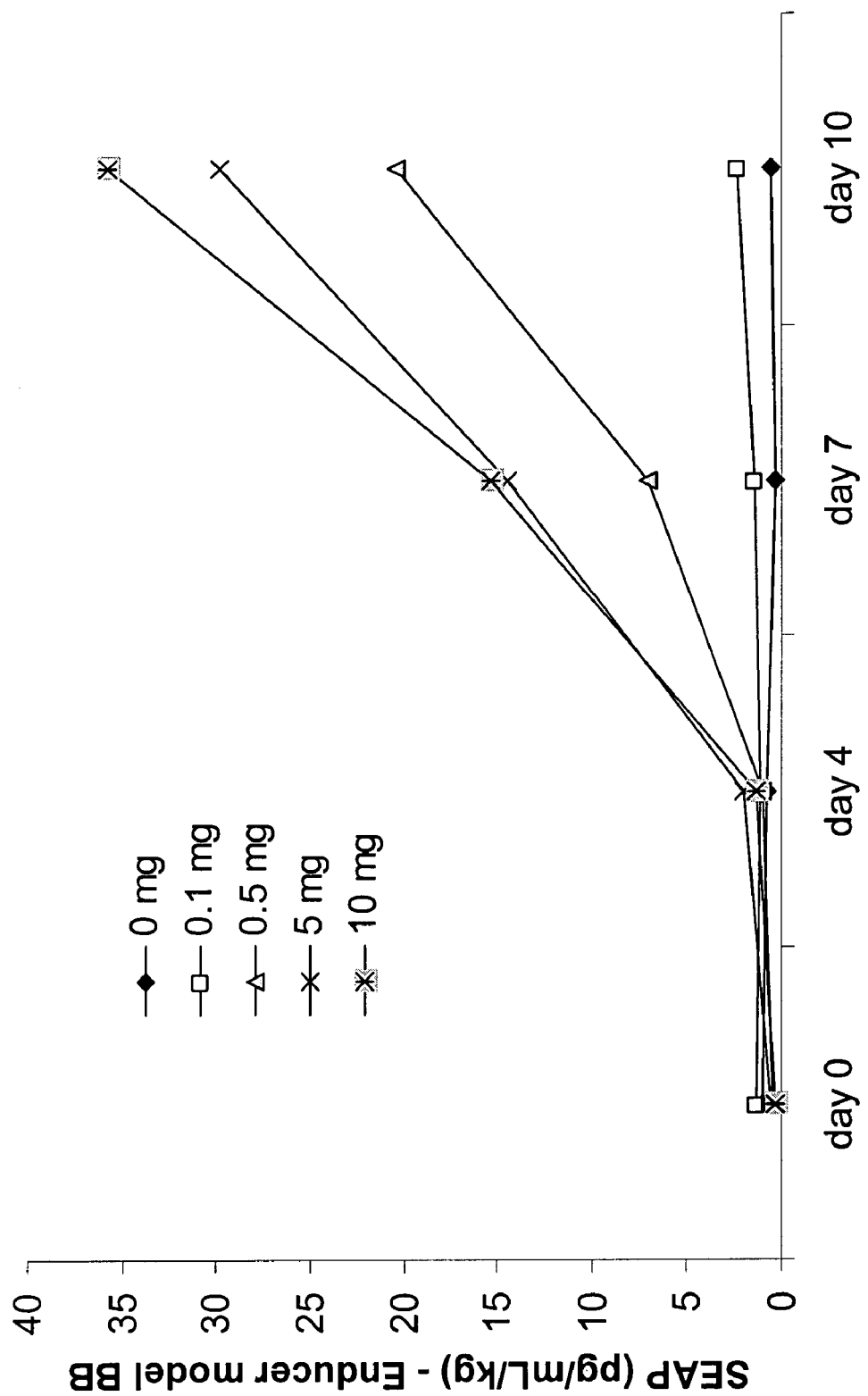

CONSTANT CURRENT ELECTROPORATION DEVICE AND METHODS OF USE

This is a continuation-in-part of U.S. patent application Ser. No. 10/360,768, "Constant Current Electrode Assembly for Electroporation," filed Mar. 7, 2002 now U.S. Pat. No. 7,245,963, the entire content of which is hereby incorporated by reference.

BACKGROUND

The present invention relates to an electroporation device and its use for facilitating the introduction of a macromolecule into cells of a selected tissue in a body or plant. The electroporation device comprises an electro-kinetic device ("EKD") which provides a series of programmable constant-current pulse patterns between electrodes in an array, user control and input of the pulse parameters, and storage and acquisition of data. The electroporation device also comprises a replaceable, or exchangeable, electrode disk having an array of needle electrodes, a central injection channel for an injection needle, and a removable guide disk.

Plasmid transfer technology has traditionally been limited in scope because in vivo expression levels resulting from the naked DNA transfer have been low, only fractions of that achieved by viral gene transfer. Numerous investigators have outlined the safety and toxicological concerns with injecting viruses as DNA vectors into animals and humans (Pilaro and Serabian, 1999). Consequently, direct injection of plasmid DNA has become more attractive as a viable alternative. Persistent plasmid DNA transfer is accomplished with the application of a series of electric pulses to drive the DNA into a stable, non-dividing, population of cells. Skeletal muscle cells have provided an ideal target for direct plasmid transfer for DNA vaccines and other applications (Mor and Eliza, 2001; Stoll and Calos, 2002). Enhancement of plasmid delivery using electroporation allows the injected muscle to be used as a bioreactor for the persistent production and secretion of proteins into the blood stream. The expression levels are increased by as much as two to three orders of magnitude over plasmid injection alone, to levels comparable to those of adenoviral-mediated gene delivery and may in some cases reach physiological ranges.

The method of plasmid delivery in vivo, termed electroporation, electro-permeabilization, or electrokinetic enhancement, is simple, efficient and reproducible. It has become valuable for basic research, with great potential for gene transfer and DNA vaccination. Electroporation has been used very successfully to transfect tumor cells after injection of plasmid or to deliver the anti-tumor drug bleomycin to cutaneous and subcutaneous tumors in humans. Electroporation has been extensively used in mice, rats, dogs and pigs to deliver therapeutic genes that encode for a variety of hormones, cytokines, enzymes or antigens. The numerous tissues and organs that have been targeted include liver, skin, eye, testis, cardiac muscle, smooth muscle, tumors at different locations, and skeletal muscle.

Broadly, electroporation is the use of a transmembrane electric field pulse to induce microscopic pathways (pores) in a bio-membrane. These pores are commonly called "electropores." Their presence allows macromolecules, ions, and water to pass from one side of the membrane to the other. Thus, electroporation has been used to introduce drugs, DNA or other molecules into multi-cellular tissues, and may prove to be effective for the treatment of certain diseases. However, the use of electroporation in living organisms has several problems, including cell death that results from generated heat and the inability of electropores to reseal. The beneficial effects of the drug or macromolecule are extremely limited with prior art electroporation methods where excessive cell heating and cell death occurs.

To better understand the process of electroporation, it is important to look at some simple equations. When a potential difference (voltage) is applied across the electrodes implanted in a tissue, it generates an electric field ("E"), which is the applied voltage ("V") divided by the distance ("d") between the electrodes.

$$E=V/d$$

The electric field intensity E has been a very important value in prior art when formulating electroporation protocols for the delivery of a drug or macromolecule into the cell of the subject. The field intensity is inversely proportional to the distance between the electrodes in that given a voltage, the field strength increases as the distance between the electrodes is decreased. However, a caveat is that an electric field can be generated in a tissue with insulated electrodes (i.e. flow of ions is not necessary to create an electric field). Although not wanting to be bound by theory, it is the flow of ions that opens the electropores and allows movement of molecules into the cells of a subject during electroporation. The flow of electric charge in a conductor or medium between two points having a difference in potential is called the current. The current between electrodes is achieved by the ions or charged particles in the tissues, which can vary among tissues and patients. Furthermore, the flow of conducting ions in the tissue can change between electrodes from the beginning of the electric pulse to the end of the electric pulse.

When tissues have a small proportion of conducting ions, resistance is increased, heat is generated and cells are killed. Ohm's law expresses the relationship between current ("I"), voltage ("V"), and resistance ("R"):

$$R=V/I$$

The resistance in the tissue between two electrodes varies depending on the charged particles present therein. Thus, the resistance in the tissue changes from the beginning of the electric pulse to the end of the electric pulse.

Heating is the product of the inter-electrode impedance (i.e. combination of resistance and reactance and is measured in ohms), and is proportional to the product of the current, voltage and pulse duration. Heating can also be expressed as the square of the current, and pulse duration ("t", time). For example, during electroporation the heating or power ("W", watts) generated in the supporting tissue can be represented by the following equation:

$$W=I^2Rt$$

Broadly, prior art teaches that metallic electrodes are placed in contact with tissues and short pulses of predetermined voltages are imposed on the electrodes initiating the cells to transiently open membrane pores. The protocols currently described for electroporation are defined in terms of the resulting field intensities E, which are dependent on short pulses of voltage proportional to the distance between the electrodes, and regardless of current. Accordingly, the resistance or heating cannot be determined for the electroporated tissue, which leads to varied success with different pulsed voltage electroporation protocols. Certainly, the difference in upper limit amplitudes of a voltage pulse between electroporation protocols that facilitate effective electroporation and electroporation protocols that cause the cells to die are very small. Additionally, a definite correlation has been observed between death of cells and the heating of cells caused by the upper limit amplitudes of the short voltage pulses. Thus, the over heating of cells between across electrodes serves as a principal cause for the ineffectiveness of any given electroporation voltage pulsing protocol. Furthermore, the current between electrodes serves as a primary determinant of the effectiveness of any given pulsing protocol, not the voltage across the electrodes.

When electricity is delivered to the cells of a subject, the dose of electricity can be accurately described in terms of charge ("Q"), which is the current ("I") and the time ("t"), according to the formula:

$$Q=It$$

If the current is not constant, as is the case in prior art electroporators, Q represents the time integral of I. In this respect, charged particles, be they ions or molecules, behave in a similar fashion. For example, when silver ions are deposited on an electrode to define the standard unit of electrical charge (the coulomb), only the charge, as defined above, is of importance. A certain minimum voltage must be present to generate a current, but the quantity of ions deposited can not be determined from a pre-determined voltage. Correspondingly, the quantity of charged particles delivered to cells in an electroporator can not be derived from the voltage imposed on the electrodes.

Although electroporation is widely used for laboratory gene transfection and gaining increased importance for non-viral gene therapy, it is generally employed using trial-and-error optimization schemes for lack of methods to predict electroporation's effects on cells (Canatella and Prausnitz, 2001). For example, it has been shown that the efficiency of plasmid gene transfer to skeletal muscle can be significantly improved by the application of an electrical field to the muscle following injection of plasmid DNA. However, this electrotransfer is associated with significant muscle damage that may result in substantial loss of transfected muscle fibers (McMahon et al., 2001). The reduction of the voltage used in the technique can result in a decrease in muscle damage, with a concomitant reduction in expression, but without a significant decrease in the number of transfected fibers.

The effectiveness of electroporation is limited by the fact that there is a threshold value for the pulse intensity below which electroporation does not occur, and an upper limit above which the cells are destroyed. Experimental evidence shows that the difference between the upper and lower limits is so small that it is very difficult to design effective pulsing protocols without undue experimentation. This makes use of the technique difficult.

References in the art directed toward an electroporation apparatus illustrate the usefulness of both an electrode apparatus and an in vivo method of electroporation. Correspondingly there are many U.S. Patents that claim either specific electrodes, or methods for electroporation. For example, U.S. Pat. No. 6,302,874 is a method and apparatus for electrically assisted topical delivery of agents for cosmetic applications; U.S. Pat. No. 5,676,646; is a flow through electroporation apparatus for implanting molecules into living blood cells of a patient; U.S. Pat. Nos. 6,241,701 & 6,233,482 describe a method and apparatus for electroporation mediated delivery of drugs and genes. More specifically, they describe a method and apparatus for electroporation therapy ("EPT") for treating tumors with a combination of electroporation using the apparatus of the invention and a chemotherapeutic agent to produce regression of tumors in vivo; U.S. Pat. No. 6,216,034 describes a method of programming an array of needle electrodes for electroporation therapy of tissue; U.S. Pat. No. 6,208,893 describes an electroporation apparatus with a connective electrode template; U.S. Pat. No. 6,192,270 describes an electrode assembly for an apparatus and a method of trans-surface molecular delivery; U.S. Pat. No. 6,181,964 describes a minimally invasive apparatus and method to electroporate drugs and genes into tissue. Using EPT as described in the invention, tumors treated by a combination of electroporation using the apparatus of the invention and a chemotherapeutic agent caused regression of tumors in vivo. U.S. Pat. No. 6,150,148 describes an electroporation apparatus for control of temperature during the process, by generating and applying an electric field according to a user-specified pulsing and temperature profile scheme; U.S. Pat. No. 6,120,493 describes a method for the introduction of therapeutic agents utilizing an electric field electroporation apparatus; U.S. Pat. No. 6,096,020 describes an electroporation method and apparatus for generating and applying an electric field according to a user-specified pulsing scheme; U.S. Pat. No. 6,068,650 describes a method of selectively applying needle array configurations for in vivo electroporation therapy; and U.S. Pat. No. 5,702,359 describes an electrode apparatus for the application of electroporation to a portion of the body of a patient with a sensing element for sensing a distance between the electrodes and generating a distance signal proportionate to the distance between said electrodes, and means responsive to said distance signal for applying pulses of high amplitude electric signal to the electrodes proportionate to the distance between said electrodes. All of these cited patents are hereby incorporated by reference.

Significant progress in the enhancement of plasmid expression in vivo and the achievement of physiological levels of a secreted protein has been recently obtained using electroporation (Draghia-Akli et al., 2002). Studies show that injection of a plasmid that expresses growth hormone releasing hormone ("GHRH"), followed by electroporation, is scalable and represents a promising approach for stably producing secreted proteins for treating large mammals (Draghia-Akli et al., 2003a; Draghia-Akli et al., 2003b). Despite the recent advances in naked plasmid delivery (Dean et al., 2003; Fattori et al., 2002), additional improvements in electroporation techniques are needed.

Previous investigators have utilized electroporation devices for plasmid DNA transfer, all of which are conceptually based on constant voltage systems, utilizing a predetermined voltage between the electrodes. Because the impedance between electrodes that are embedded in a tissue can vary from case-to-case, or tissue-to-tissue, a predetermined voltage does not produce a predetermined current. A predetermined voltage pulse causes an unregulated increase in the current flowing through a muscle tissue during the duration of the pulse in addition to the loss of the perfect square wave function. By contrast, a constant-current source actually maintains a square wave function constant current through muscle tissue. However, the existing commercial electroporation devices do not have the firmware design to enable measurement of the exact amount of current to which the cells are exposed. The unregulated current generated with conventional electroporation devices may generate amounts of heat in tissues that can easily kill cells (Martin et al., 2002; Pliquett et al., 2002). For example, a typical electronic 50 milliseconds (ms) pulse with an average current of 5 Amperes (A, or Amp) across a typical load impedance of 25 ohms ($\Omega$) can theoretically raise the temperature in tissue 7.5° C., which is enough to kill cells. The physics of tissue injury caused by electrical shock is reviewed by Lee et al. (Lee et al., 2000). By contrast, the power dissipation is less in a constant-current system and controls heating of a tissue, which may reduce tissue damage and contribute to the overall success of the procedure. Thus, there is a need to avoid the technological problems associated with constant voltage electroporation by providing a means to control effectively the amount of electricity delivered to the cells and thereby achieve proficient electroporation.

The difficulties present in prior-art electrodes stem from the fact that the pulse energy is concentrated in the center of the array, the point where the material to be transfected is deposited. As a result, the spatial distribution of energy delivery assumes a very non-uniform character. Therefore, only a fraction of the cells in the volume encompassed by the electrode assembly is electroporated. Thus, there is also a need to provide a means to effectively control the dosage of electricity delivered to the cells in the inter-electrode space by precisely controlling the ionic flux that impinges on the conduits in the cell membranes.

Furthermore, commercially available electroporation devices and needle arrays typically do not permit injection and electroporation in one combined operation. With these instruments, the procedure requires that the injection needle be inserted into the target muscle for plasmid delivery, and then removed. Subsequently, the electrodes are inserted into the muscle in the proximity of the injected area, usually identified by a skin tattoo. However, the underlying muscle may more or contract so the injection site may not be completely circumscribed by the needle electrodes. Thus, there is a need for an electroporation device that permits injection and electroporation in one combined operation so that the needle electrodes delineate the injection area during the entire electroporation procedure.

In addition, electroporation devices which use skin and muscle invasive replaceable needle arrays as electrodes to deliver the electric current require maintenance of sterile conditions when the needle array replacement occurs. This is necessary from both a medical practice and regulatory compliance viewpoint. Typically, if there is an orifice in the electroporator handle and electrode disk through which the injection needle must pass to deliver solutions to the tissue, the orifice is not sterile. Depending on the skill of the operator, the injection needle may or may not touch the non-sterile surfaces of the orifice. Furthermore, replacement of the electrode disk is typically done manually, risking contamination of the needle array. Thus, there is also a need to provide an electrode disk that allows delivery of the medicinal solution and replacement of the needle array under sterile conditions.

SUMMARY

The present invention pertains to an electroporation device and its use for facilitating the introduction of a macromolecule into cells of a selected tissue in a body or plant. The electroporation device comprises an electroporation enducer, or electro-kinetic device ("EKD"), which provides constant current to produce an electric field and has hardware which enables the user, through a controller, such as a single-chip microcontroller and a software or firmware application, to control the electric pulse parameters and to document the electrical features of each pulse. The present invention also pertains to a replaceable, or exchangeable, electrode disk comprising an array of needle electrodes mounted on a support structure having a central injection channel, or central port, for an injection needle. The central channel allows an injection needle to be inserted simultaneously with the insertion of the needle electrodes to allow both sterile delivery of the medicinal solution and delineation of the injection area by the electrodes. A guide disk of variable thickness is also provided for the electrode disk, allowing the operator to control the depth of penetration of the needle electrodes and replace the electrode disk without touching the sterile needles.

The electroporation device and the EKD can be used to electroporate cells and deliver plasmid DNA without causing permanent damage to adjacent cells. Furthermore, use of the electroporation device causes an increase in electroporation efficiency, meaning that a smaller amount of plasmid is needed to generate adequate levels of target proteins.

The electro-kinetic device ("EKD") provides a constant-current electric field through the electrode needle array in various user-programmable pulse patterns and facilitates the introduction of a macromolecule into cells of a selected tissue in a body or plant. The EKD comprises an electrode assembly having a plurality of needle electrodes; a current waveform generator for applying a pattern of constant-current pulses or a current pulse train waveform that runs through the electrode array; a power source; a controller for controlling the operation of the current waveform generator and other peripheral devices; and a waveform logger for recording the electroporation voltage and current waveforms that are generated. The controller of the EKD operates through a software or firmware application which enables users to input desired parameters and control the operation of the EKD. The EKD may also include an impedance tester for optional monitoring of the amount of resistance in the target tissue. Other components of the EKD may include: an input device for inputting operating parameters; a status-reporting device for reporting status information; a communications port; memory; and a power switch. Another aspect of the EKD is the electrode assembly, which preferably includes a non-conductive handle. The electrode handle assembly contains the needle electrode array and may contain a status-reporting device and an activation switch. The handle assembly may also be adapted to receive the replaceable electrode disk.

The central channel, or port, of the electrode disk allows the user to inject the medicinal solution and electroporate the tissue area in one operation, which ensures that the injection area will be delineated by the needle electrodes. The electrode disk also eliminates cross-contamination between subjects in a group receiving injectable solutions accompanied by electroporation with the same equipment. Each disk can be sterilized, inserted into the handle by grasping the guide disk, and used to inject the medicinal solution through the central channel without risk of contamination of either the injection needle or the electrodes.

The EKD produces a constant current pulse train waveform that sequences between at least any two electrodes of the needle electrode assembly. The EKD can deliver a decentralized constant-current pulse to an area of a tissue such that electroporation overlap points do not develop. Furthermore, the utilization of a constant-current pulse has several advantages over prior art, one advantage being reduced heating and subsequent death of the electroporated tissue. The present invention also allows the entire modular electrode system to be portable and operated via a battery pack.

The present invention also pertains to a method for facilitating the transport of a macromolecule into cells of a selected tissue in the body or plant. Briefly, an operator can firmly insert the plurality of needle electrodes into the selected tissue in a body or plant. In preferred embodiments, the needle electrodes are part of the replaceable electrode disk. The removable guide disk may be used to control the depth of penetration of the needle electrodes. An injection needle may then be passed through the sterile central channel of the electrode disk. The macromolecules are delivered via the injection needle into the selected tissue. The EKD is activated, an electroporation sequence is entered, and the electrode-firing sequence is applied to the plurality of needle electrodes. The applied constant-current electrical pulse facilitates the introduction of the macromolecule into the cell between the plurality of electrodes. Cell death due to overheating of cells is prevented by keeping the constant-current below a certain critical value. When electrode disks are replaced, they can be grasped by the guide disk to ensure continued sterility of the needle electrodes.

BRIEF DESCRIPTION OF THE DRAWINGS

FIG. 9A shows an artistic representation of current pulses and FIG. 9B shows an artistic representation of current waveform, both of which are produced by the pulse pattern of FIG. 8.

FIG. 21 shows an example of a first set of data that can be acquired and stored by the EKD during a sample electroporation procedure.

FIG. 22 shows an example of a second set of data that can be acquired and stored by the EKD during a sample electroporation procedure.

FIG. 23 shows a formatted example of a third set of data that can be acquired and stored by the EKD during a sample electroporation procedure.

FIG. 30 shows the expression levels of SEAP in animals which were injected with different amounts of plasmid pSP-SEAP and electroporated with an alternative electroporation device.

DETAILED DESCRIPTION OF PREFERRED EMBODIMENTS

Figure 1:
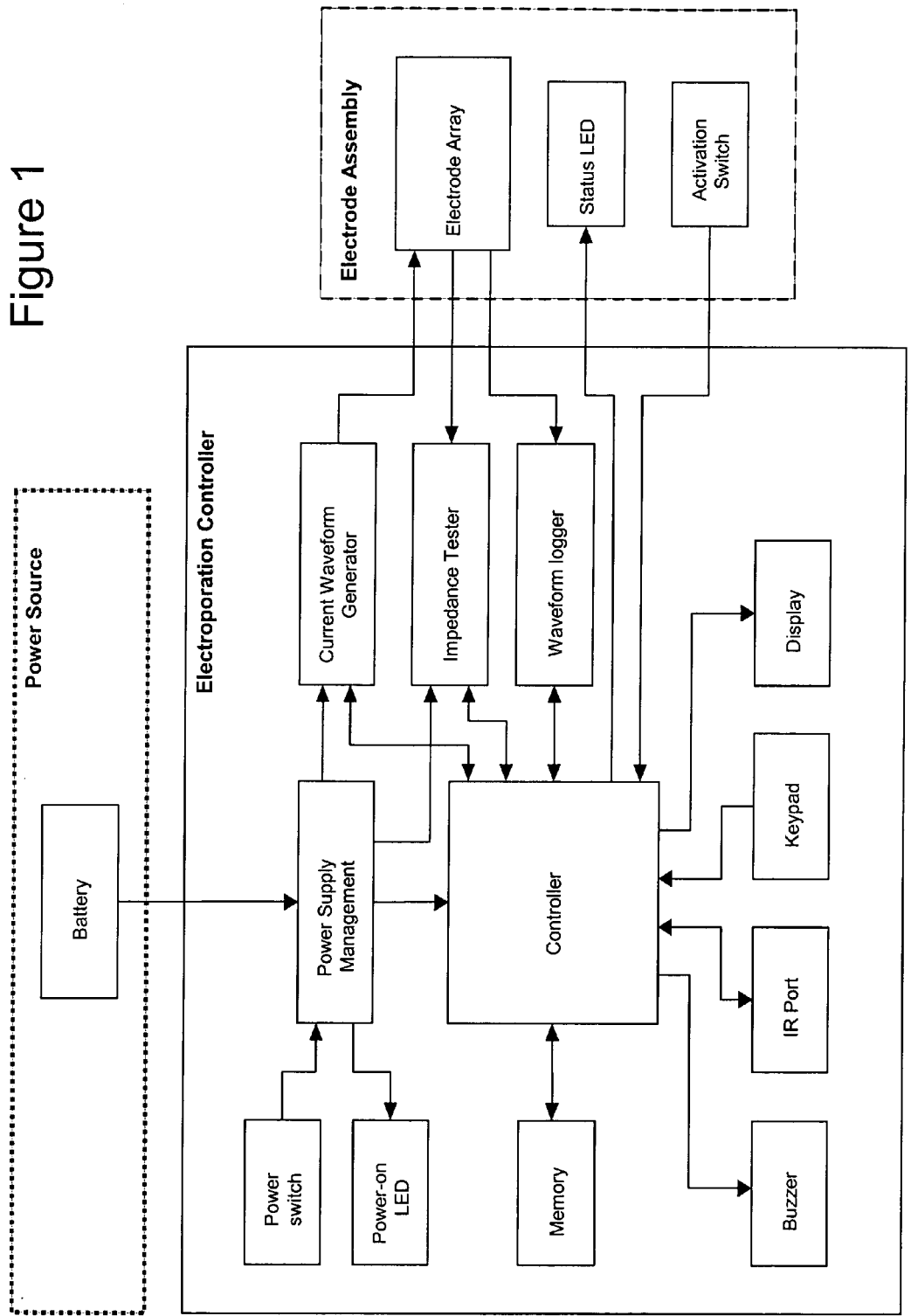
FIG. 1 shows a system diagram, or flow chart, of a preferred embodiment of the EKD.

The term "current" as used herein refers to the flow or rate of flow of electric charge in a conductor or medium between two points having a difference in potential, generally expressed in amperes.

The term "ampere" as used herein refers to the standard unit for measuring the strength of an electric current. It is the rate of flow of charge in a conductor or conducting medium of one coulomb per second.

The term "coulomb" as used herein refers to the meter-kilogram-second unit of electric charge equal in magnitude to the charge of $6.28 \times 10^{18}$ electrons or the charge transported through a conductor by a current of one ampere flowing for one second.

The term "voltage" as used herein refers to the electromotive force, or difference in electrical potential, expressed in volts, which are the practical units of electromotive force or difference in potential between two points in an electric field that requires one joule of work to move a positive charge of one coulomb from the point of lower potential to the point of higher potential.

The term "power" as used herein refers to a source of physical or mechanical force or energy that is at, or can be put to, work, e.g. "electric power, water power."

The term "impedance" as used herein refers to the total opposition offered by an electric circuit to the flow of an alternating current of a single frequency. It is a combination of resistance and reactance and is measured in ohms.

The term "field" as used herein refers to physical quantity specified at points throughout a region of space.

The term "quick-release mechanism" as used herein refers to any connector mechanism that allows the plurality of needle electrodes to be fastened securely and released quickly from the constant-current pulse generator subsystem. When the needle electrodes are fastened securely, the quick release mechanism also maintains electrical communication with the constant-current pulse generator subsystem. Many different types of quick-release mechanisms are well known in the art of engineering.

The term "amplitude" as used herein refers to the extreme range of a fluctuating quantity, as an alternating current or the swing of a pendulum, generally measured from the average or mean to the extreme. It is the amount or degree to which a thing extends.

The term "frequency" as used herein refers to the number of periodic oscillations, vibrations, or waves per unit of time. It is usually expressed in hertz (Hz).

The term "macromolecule" as used herein refers to nucleic acid sequences, proteins, lipids, microbubbles (e.g. drug-loaded vesicles), and pharmaceuticals.

The present invention pertains to an electro-kinetic device ("EKD") for providing a constant-current electric field through an electrode needle array and facilitating the introduction of a macromolecule into cells of a selected tissue in a body or plant. The EKD produces a current pulse train waveform that passes through the electrodes of the electrode needle array in accordance with a programmed sequence and can be monitored and recorded during the procedure.

The present invention also pertains to a replaceable, or exchangeable, electrode disk having a needle array which may be used in association with an electroporation device, such as an EKD. The electrode disk has a central channel or port, through which an injection needle may be inserted to allow sterile delivery of the medicinal solution, and a removable guide disk, for controlling the depth of penetration of the needle electrodes and facilitating replacement of the disk.

FIG. 1 shows a system diagram of one preferred embodiment of the EKD. Major functional elements of the EKD are shown in the diagram. Each element is described in terms of the hardware functionality of each element. The sequences of events that are enabled by the hardware are controlled by software or firmware, as described below.

The central element of the EKD is the controller, which is responsible for controlling various peripheral devices connected to it. The controller is responsible for managing the electroporation procedure, which includes operations such as: (1) Generating the electroporation firing sequence or constant-current pulse pattern for the electrode assembly by controlling the current waveform generator; (2) Performing impedance testing to determine if electroporation should be performed; (3) Sensing and processing user commands; (4) Providing the user with status information; (5) Transmitting electroporation data to an external electronic device via the communications port; and (6) Saving and retrieving electroporation data (e.g. voltage and current curves) to and from memory.

Figure 2:
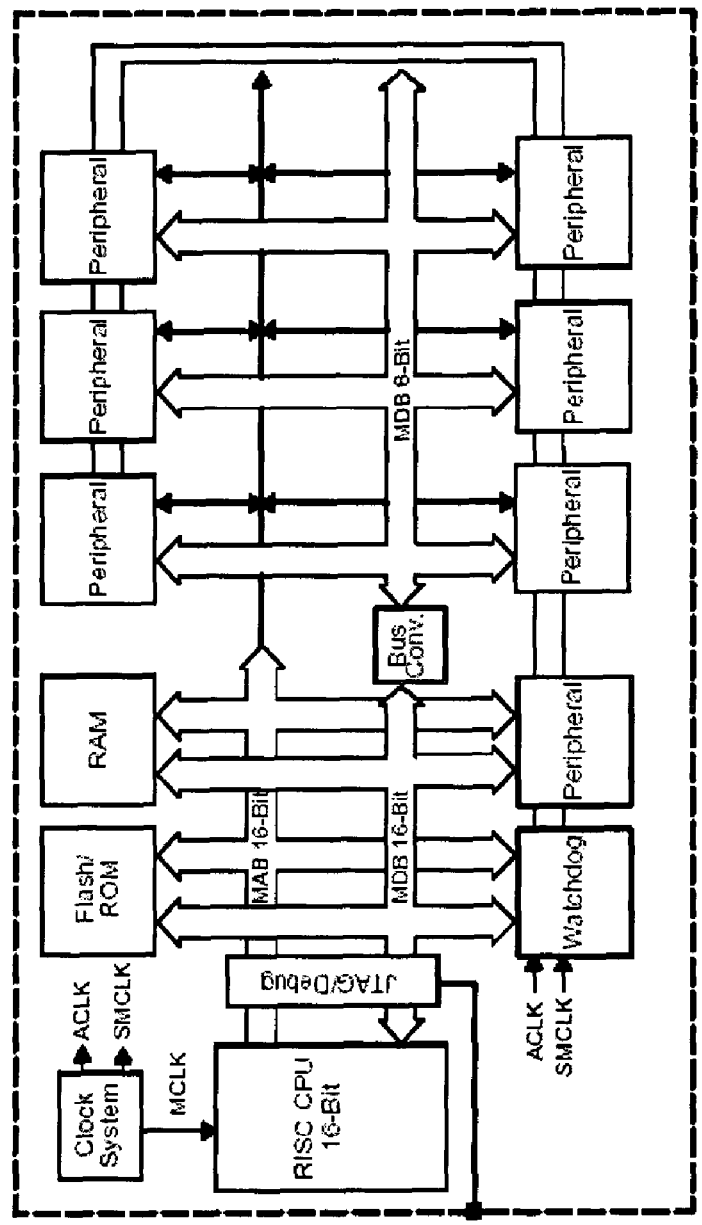
FIG. 2 shows an example of a controller which may be used in the EKD.

The controller is preferably a single-chip microcontroller (such as, Texas Instruments msp430F149, or Motorola 68HC908AZ60A), such as the microcontroller shown in FIG. 2. The boxes labeled "Peripheral" in FIG. 2 represent any of the peripheral devices of the EKD which are shown in FIG. 1 and discussed below. The software directing the steps of the electroporation procedure is preferably firmware, because it resides permanently within and runs from the single-chip microcontroller.

Another component of the EKD is the current waveform generator. The current waveform generator generates a current pulse train waveform that passes through the electrodes of the electrode array in accordance with a programmed sequence. The pulse train is square in shape and the number of pulses is limited by the software or firmware. One pulse is applied to each electrode set. Typically, each pulse is 52 ms in duration and occurs at a rate of 1 Hz. The amplitude of the pulse train is programmable by the operator and ranges from 0.1 A to 1.5 A in increments of 0.1 A. The current waveform generator may be composed of general power-transistor analog circuits which function as directed by the controller.

An additional component of the EKD is the impedance tester. The impedance tester determines if the resistance of the load (e.g. muscle tissue) is sufficiently low. If the resistance is too high, the resulting voltage across the electrodes might be too high and cause heating and cell damage. Electroporation treatment may therefore be preceded by an impedance test. If any of the impedance measurements exceeds 100 Ω+5Ω, the impedance test fails and the electroporation sequence is not initiated. The impedance test is an operator programmable feature controlled by software or firmware that may be disabled during the operation. The impedance tester may be composed of general operational amplifier ("op-amp") analog circuits which function as directed by the controller.

The impedance tester also functions as a safety feature in the EKD in order to make it a safe device to operate. It indicates whether all of the electrodes have penetrated the same tissue and a circuit can be established. Electrodes in contact with air, especially dry air, have an extremely high resistance. If electroporation starts and one or more electrodes have not penetrated the tissue, the resulting electrode voltages can be thousands of volts, which might have lethal consequences and also damage the EKD. For this reason, overload voltage protection may be implemented to prevent excessive voltages on the electrodes. For example, regardless of the electrical load (e.g. air or muscle tissue), the overvoltage protection may be engaged if $V_{ij}$ exceeds 200V for a period of no more than 1 ms. $V_{ij}$ is the voltage across electrode i and j where i, j=1 to 5. If the over-voltage protection engages, $V_{ij}$ goes to approximately 0 V until the next electroporation pulse is fired. While the EKD is in the off state, the voltage across any electrode pair preferably does not exceed 10V.

A further component of the EKD is a waveform logger. The waveform logger records electroporation voltage and current waveforms, which are to be continuously sampled during electroporation treatment. By sampling and monitoring the parameters of the electroporation procedure, an operator can more easily analyze possible problems and adjust the settings in the event that an electroporation procedure fails or doesn't achieve desirable results. An exemplary sample rate is 2000 samples per second, about 104 samples for each of the 5 current pulses. An exemplary total sample period is 4152 ms with sampling starting approximately 50 ms before the first pulse is fired and stopping about 50 ms following the last pulse. The voltage and current waveforms may be quantified into a 12-bit digital representation with ±1 least significant bit ("LSB") linearity. The current waveform resolution should preferably be at least 5 mA and the voltage waveform resolution should preferably be at least 0.25 V. The waveform logger may be composed of general op-amp analog circuits and an analog to digital ("A/D") converter suitable for use with the controller.

Another component of the EKD is an input device for inputting user commands. For example, the EKD operating parameters may be entered by an operator via a numeric keypad (such as, Grayhill 88AB2). In a preferred embodiment, the numbers input into the keypad are displayed on a liquid crystal display ("LCD"). Typical parameters that can be programmed are the electroporation pulse current, impedance test enable/disable, and electroporation firing delay. The features related to the keypad are also directed by the controller.

Other possible components of the EKD include status-reporting devices for displaying or otherwise notifying the operator as to the status of the system. These status-reporting devices may include an information display panel, such as a liquid crystal display ("LCD") (such as, Lumex LCM- S02004DSF, or Optrex DMC-20434N). The LCD is preferably of the character display type and is preferably capable of displaying 4 lines of 20 characters each. The LCD is also preferably equipped with a back-light that can be switched on and off by means of a toggle switch. Status information may also be provided by audible notification, such as a buzzer (such as, CUI CEP-2202AS) sounding at various pitches. Each pitch preferably has a different meaning, as controlled by the software or firmware. For example, the volume of the buzzer may have 3 programmable settings and range roughly from 60 to 80 dB at a distance of 1 meter from the buzzer. The sound pressure level range is only given as reference. The sound level is deemed acceptable if it is audible in a noisy environment (e.g. a farm) if set to its highest level and it is not too loud in a quite environment (e.g. an office) if set to its lowest level. In addition, the EKD may be equipped with a light emitting diode ("LED") (such as, Lumex SSI-LXR16121D, or any panel-mount red LED) to designate whether the unit is turned on or off.

A further component of the EKD is a communications port that can be used to upload electroporation waveform data to an external electronic device, such as a personal digital assistant ("PDA") or personal computer ("PC"), for viewing purposes. Preferably, the communications port is an optical serial communications port, such as an infrared ("IR") port (such as, Transceiver: Vishay TFDU4100, or Zilog ZHX1201; Encoder: Microchip MCP2120, or TI TIR1000).

The EKD may also possess a memory component. The memory component stores electroporation waveform data and operating parameters. Preferably, the memory (such as, Atmel AT45 DB321B) is nonvolatile, meaning it retains its data even if the EKD is off. To conserve memory, electroporation waveform data may only be saved to memory during the active periods of the electroporation pulse train. During the inactive periods, sampled data may only be stored to memory if either one of the waveforms exceeds a specified threshold. For example, these thresholds may be a voltage threshold of 2 V and a current threshold of 10 mA. Data stored to memory during the inactive periods of the current pulse train may be time stamped so that the time index of the data is known once the waveforms are reconstructed. Provision may be made for the storage of up to 40 samples (20 ms) of data that occur during the inactive periods of the pulse train. Storage can be limited to 20 ms because the software can specify that the remainder of the electroporation sequence will be aborted if anyone of the thresholds is exceeded for a cumulative period of more than 20 ms. An electroporation waveform data set requires about 2 kB of memory when the above compression technique is implemented. The EKD preferably contains sufficient memory to save at least 600 electroporation waveform data sets.

Further components of the EKD are a power source and a power switch. The power source is preferably a battery (such as, 2×Powersonic PS-640 F1, or Panasonic LC-R064R2P) and is responsible for providing power to each of the EKD's circuits. These circuits include a low voltage/low power capacity power supply for the controller and its peripherals, a low voltage and low power capacity power supply for the impedance tester, and a high power capacity power supply for the current waveform generator. The power switch (such as, E-Switch R5CBLKBLKEF0, or any DPDT 10A panel-mount rocker switch) controls power to the EKD and can be either on or off. In the off position, all electrical connections to the electrode assembly are electrically neutral within 5 seconds after power is turned off.

The EKD also includes an electrode handle assembly. Preferably, the electrode handle assembly includes three elements: a needle electrode array, a status-reporting device for reporting the status of the EKD, and an activator switch. In a preferred embodiment, the needle electrode array is circular and comprises five needle electrodes. The status of the EKD is preferably indicated on the handle assembly through the use of one or more LED's, which can be in varying colors and programmed to flash intermittently to signify various steps of the electrode firing sequence. The handle assembly activator switch is preferably used to initiate various steps of the electrode firing sequence.

Figure 3:
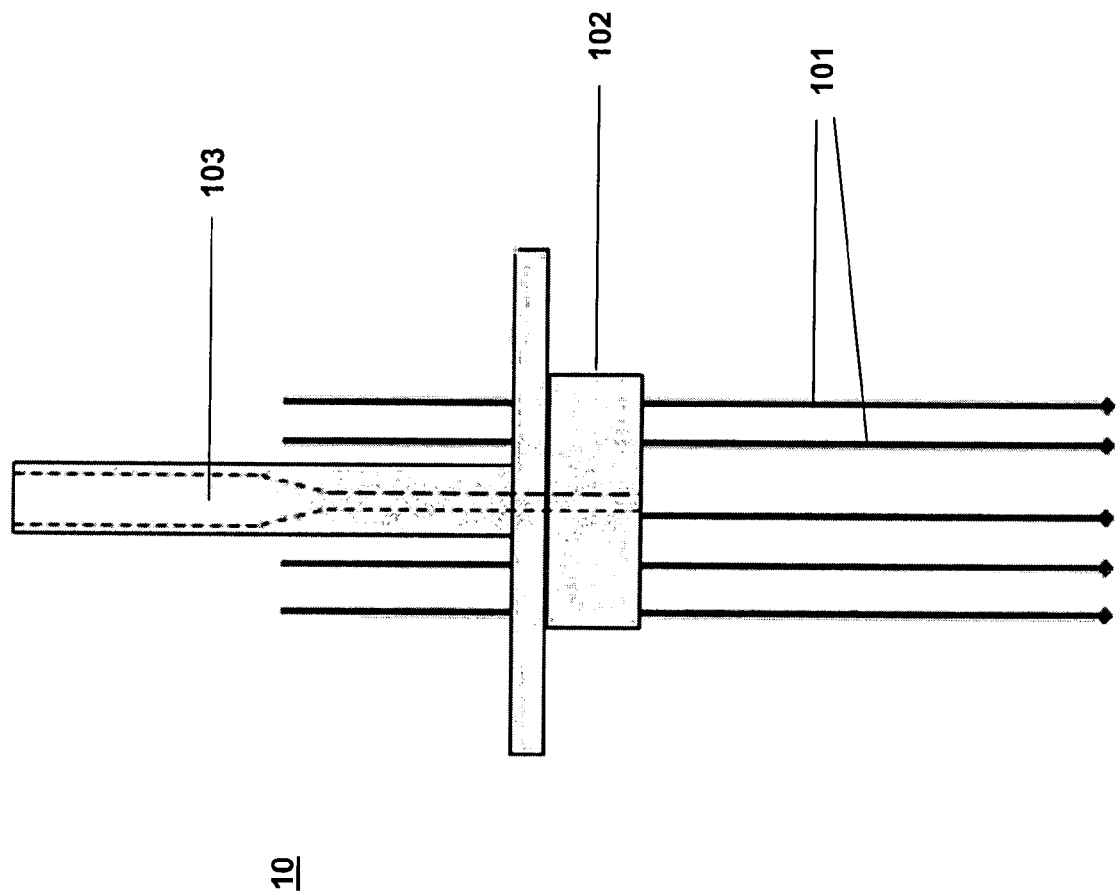
FIG. 3 shows a side view of the replaceable electrode disk.
Figure 4:
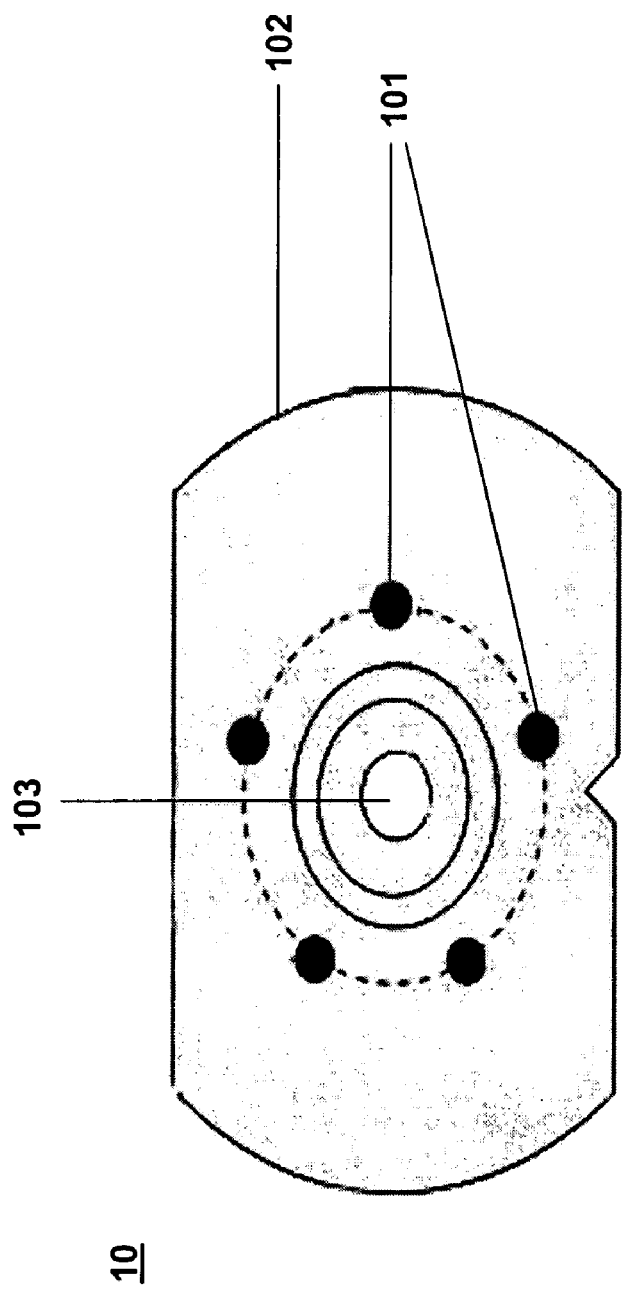
FIG. 4 shows a top view of the replaceable electrode disk.

Another embodiment of the present invention is a replaceable electrode disk which may be removably mounted in the handle of an electroporation device. In a preferred embodiment, the replaceable electrode disk is mounted in the electrode handle assembly of the EKD. FIG. 3 shows a side view of the electrode disk and FIG. 4 shows a top view of the electrode disk. In FIGS. 3 and 4, the electrode disk 10 has a plurality of needle electrodes 101 mounted on a support structure 102 in a spatial arrangement for penetrating the selected tissue. In a preferred embodiment, the spatial arrangement is a circular array. Individual electrodes in the needle array on the handle side of the electrode disk are blunt-ended and deburred for insertion into the complementary electrical contact fittings in the handle. The handle preferably houses an electrical connector from the needle electrodes to the pulse generator or EKD. The electrode disk support structure 102 also has a sterile central injection channel 103 (shown in dotted lines), through which an injection needle may be passed for injection of the macromolecules. The channel 103 preferably extends outward on the top side of the electrode disk 10, through the support structure 102 and handle, to a sufficient length to create a sterile tube that passes through both the handle and disk. Thus, the handle provides a user an easy means for implanting the needle electrodes into a selected tissue and contemporaneously injecting the macromolecules.

Figure 5:
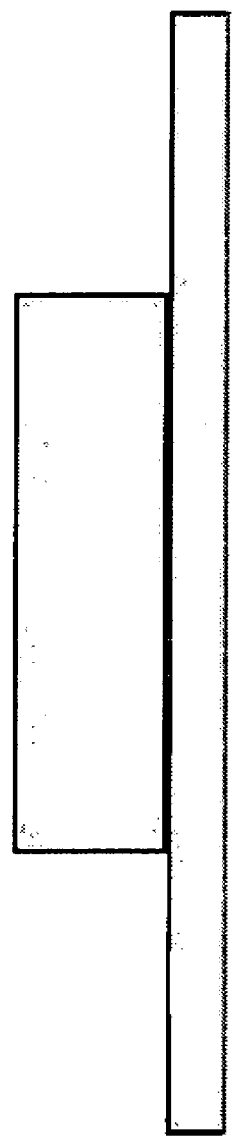
FIG. 5 shows a side view of the guide disk.
Figure 6:
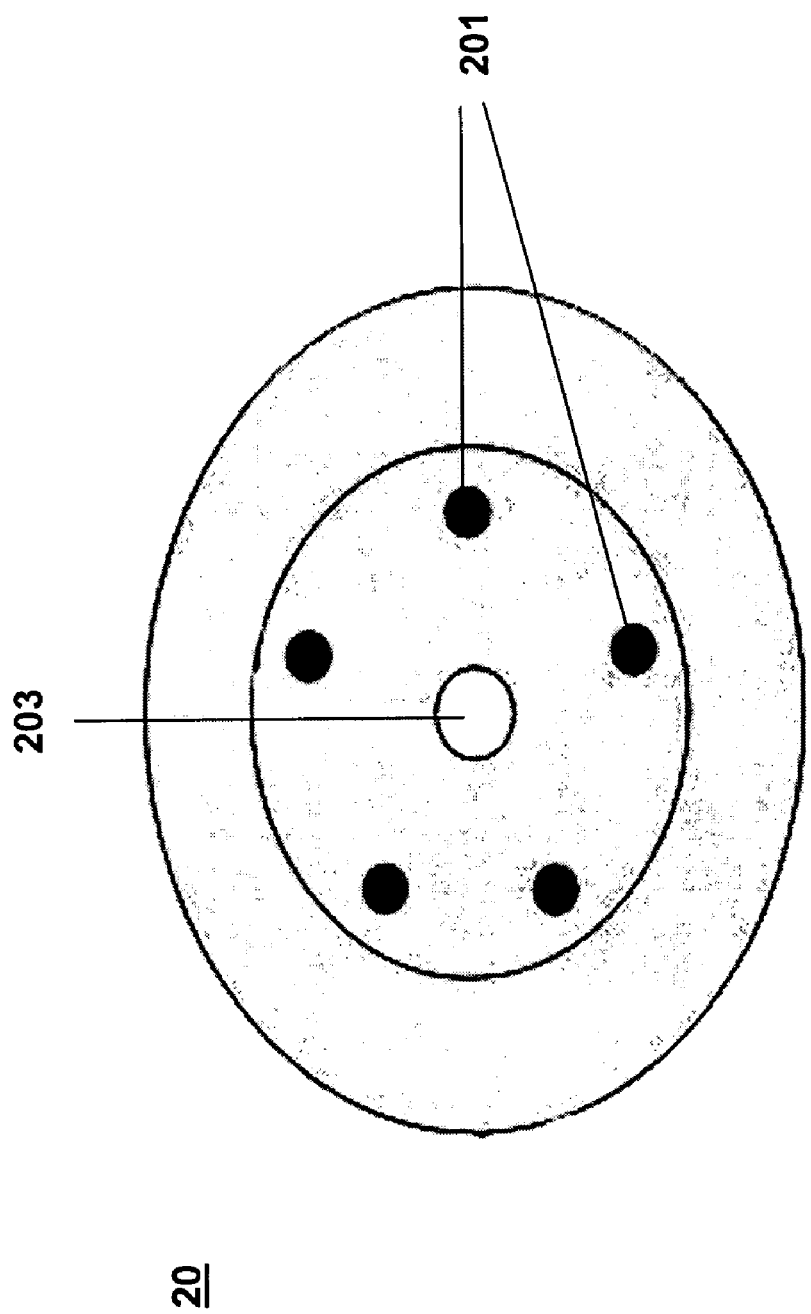
FIG. 6 shows a top view of the guide disk.
Figure 7:
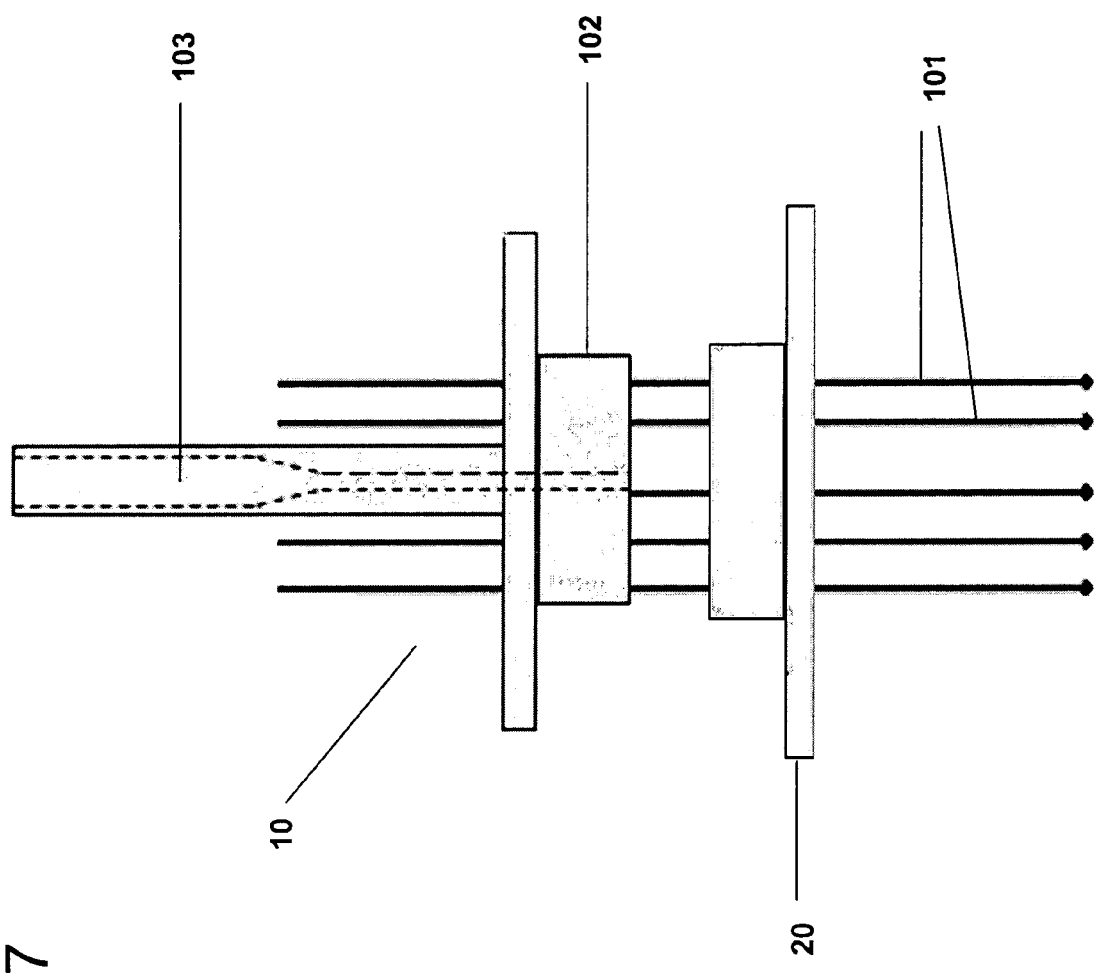
FIG. 7 shows a side view of the guide disk mounted on the replaceable electrode disk.

A guide disk which can be mounted on the replaceable electrode disk is also provided. FIG. 5 shows a side view of the guide disk and FIG. 6 shows a top view of the guide disk. As shown in FIGS. 5 and 6, the guide disk 20 has a plurality of guide holes 201 corresponding to the physical spacing of the needle electrodes 101 (FIGS. 3 and 4) and a central passage 203 corresponding to the central channel 103 (FIGS. 3 and 4) of the electrode disk for the insertion of the injection needle. The guide disk may be of variable thickness, allowing the operator to control the depth of penetration of the needle electrodes. The guide disk also allows the operator to replace the electrode disk without touching the sterile needles. FIG. 7 shows the guide disk 20 mounted on the electrode disk 10.

In a preferred embodiment, the needle electrodes in the EKD electrode assembly as well as in the replaceable electrode disk are in a circular array. In a further preferred embodiment, the plurality of needle electrodes consists of five needle electrodes. In an additional preferred embodiment, the centers of the five needle electrodes fall in a circular array in the shape of a pentagon inscribed by roughly a 1.0 cm diameter circle.

Figure 8:
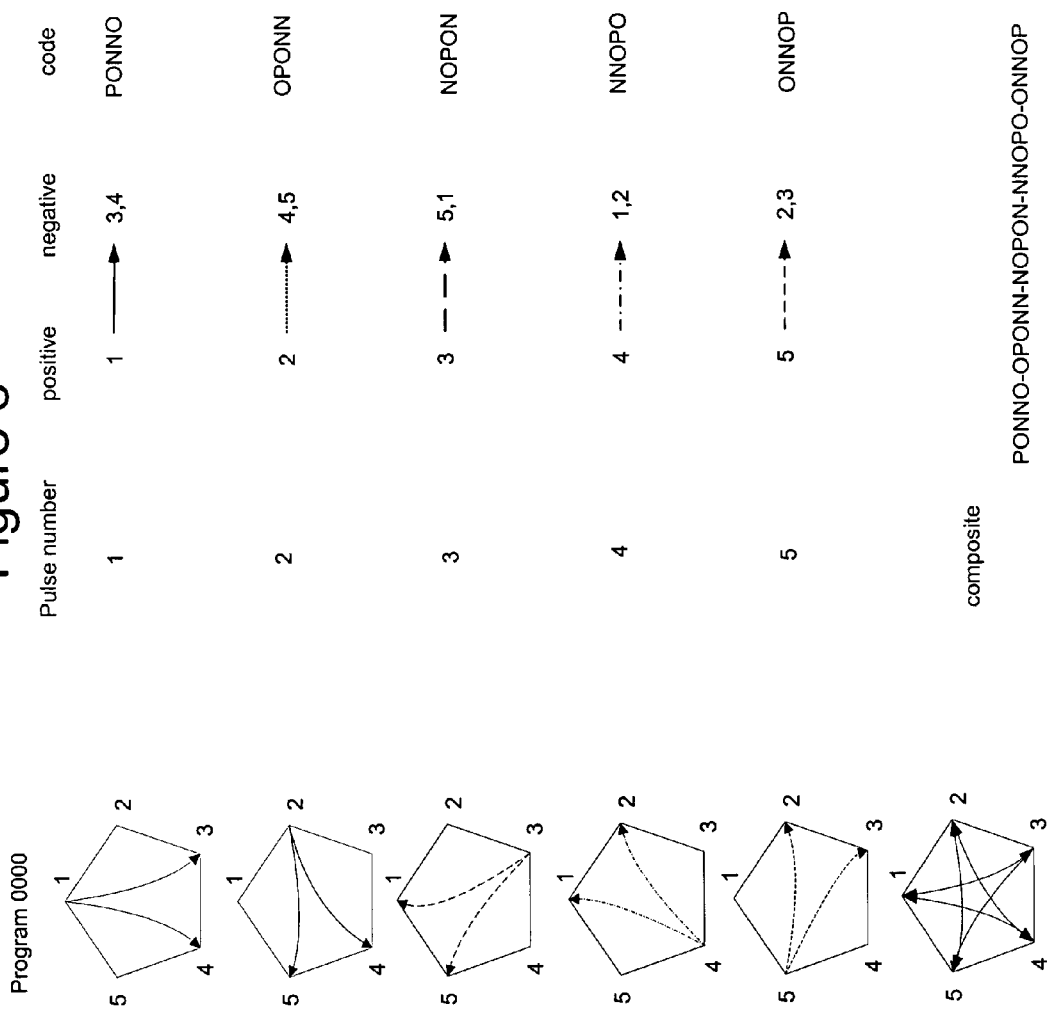
FIG. 8 shows an example of a programmed electrode pulse pattern, labeled Program 0000, for the EKD.
Figure 10:
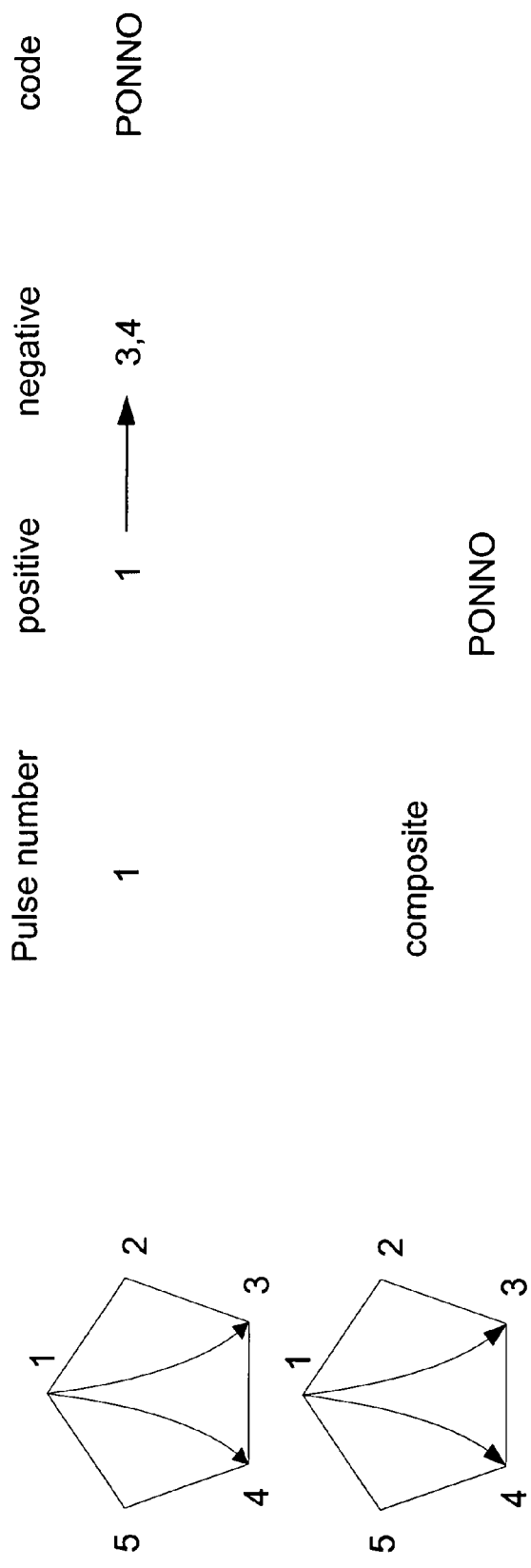
FIG. 10 shows an example of a programmed electrode pulse pattern, labeled Program 0001, for the EKD.
Figure 11:
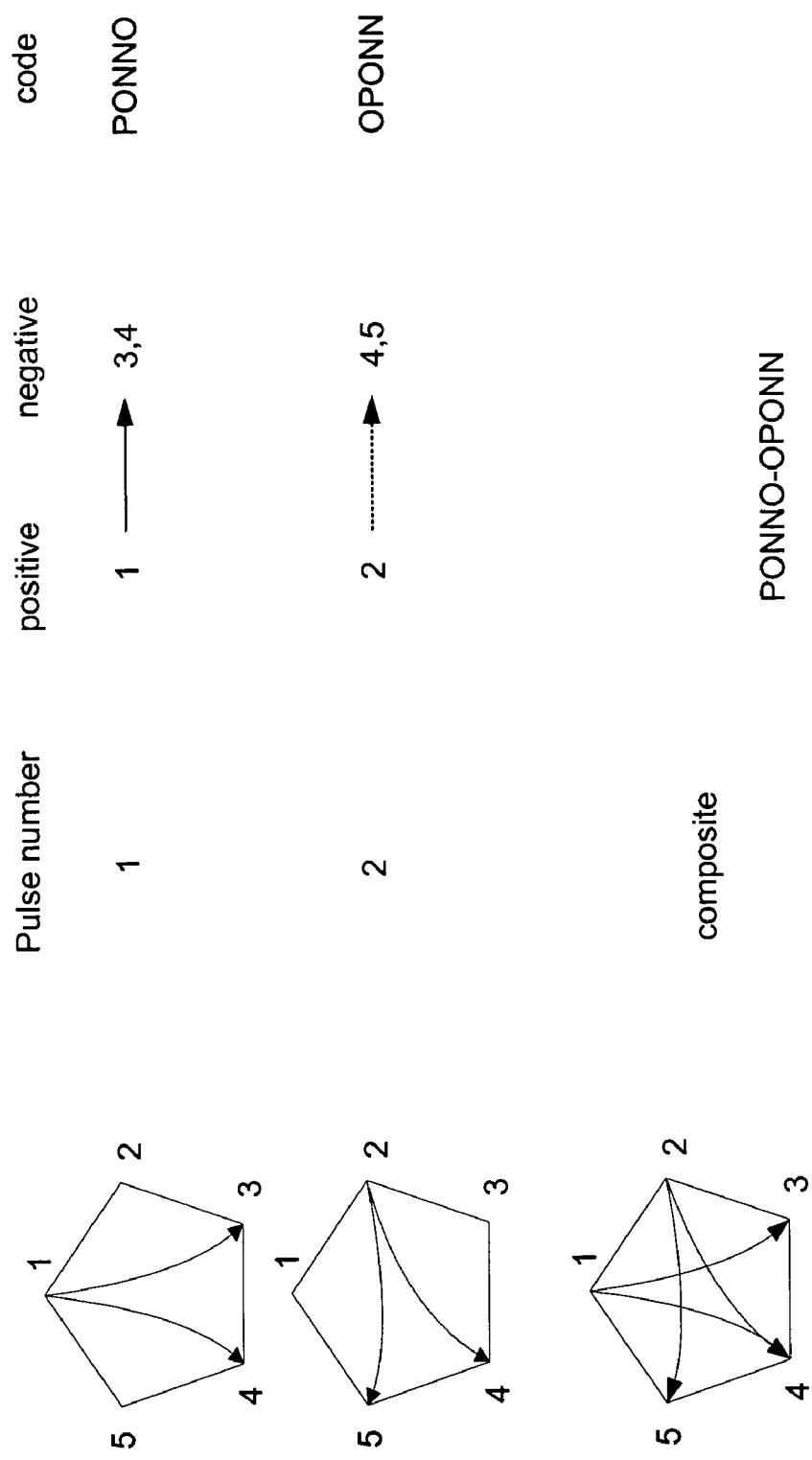
FIG. 11 shows an example of a programmed electrode pulse pattern, labeled Program 0002, for the EKD.
Figure 12:
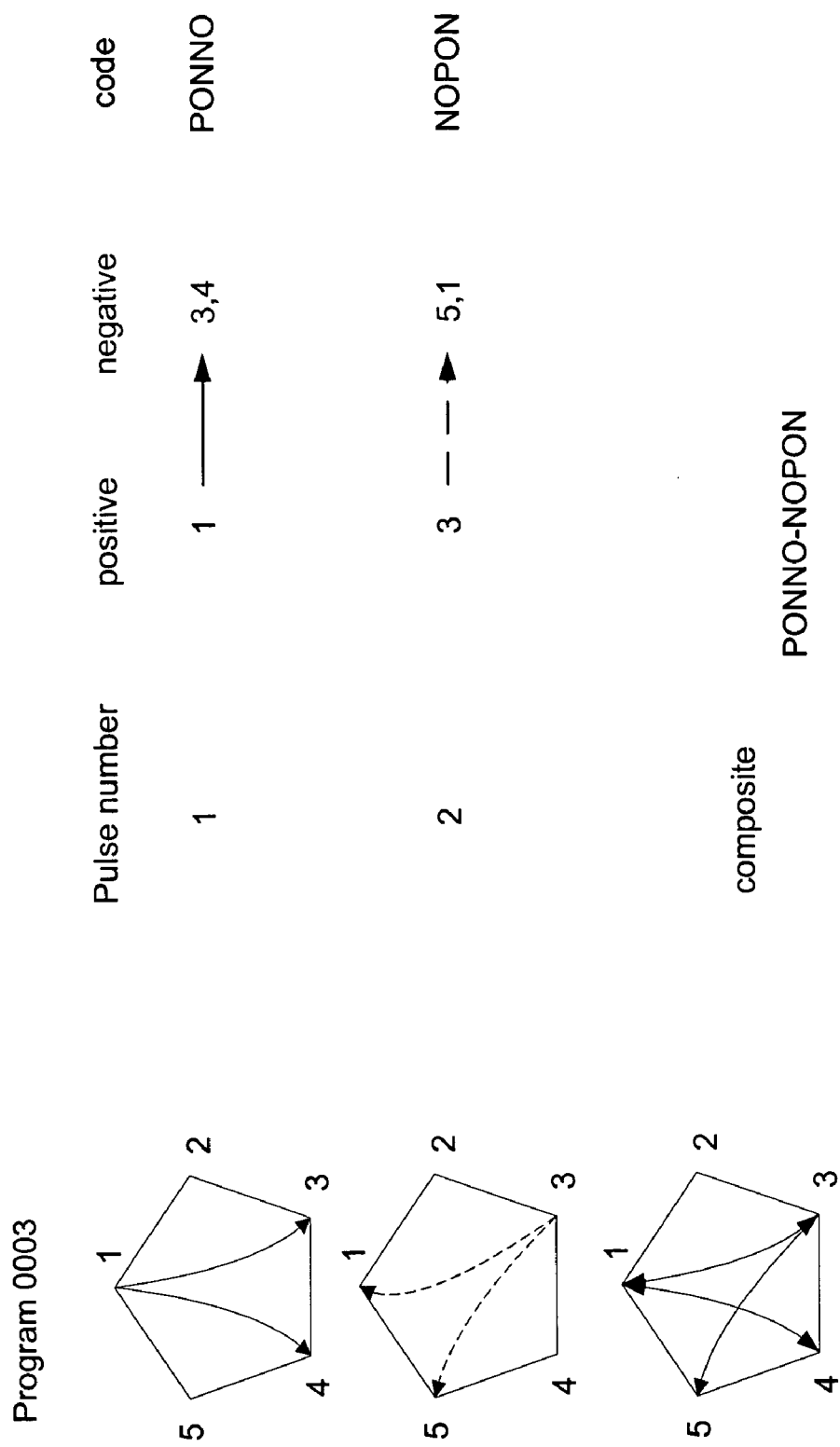
FIG. 12 shows an example of a programmed electrode pulse pattern, labeled Program 0003, for the EKD.
Figure 13:
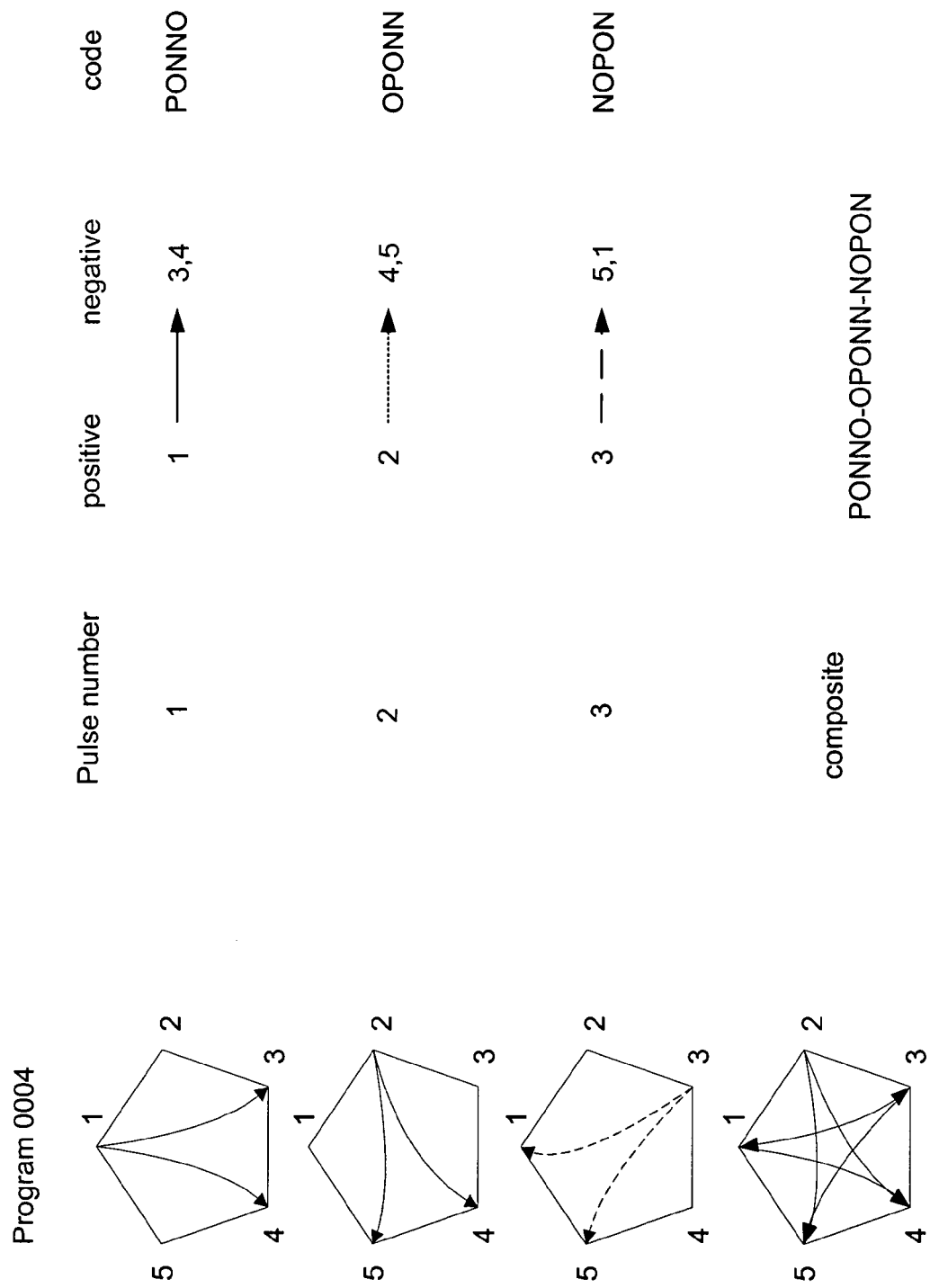
FIG. 13 shows an example of a programmed electrode pulse pattern, labeled Program 0004, for the EKD.
Figure 14:
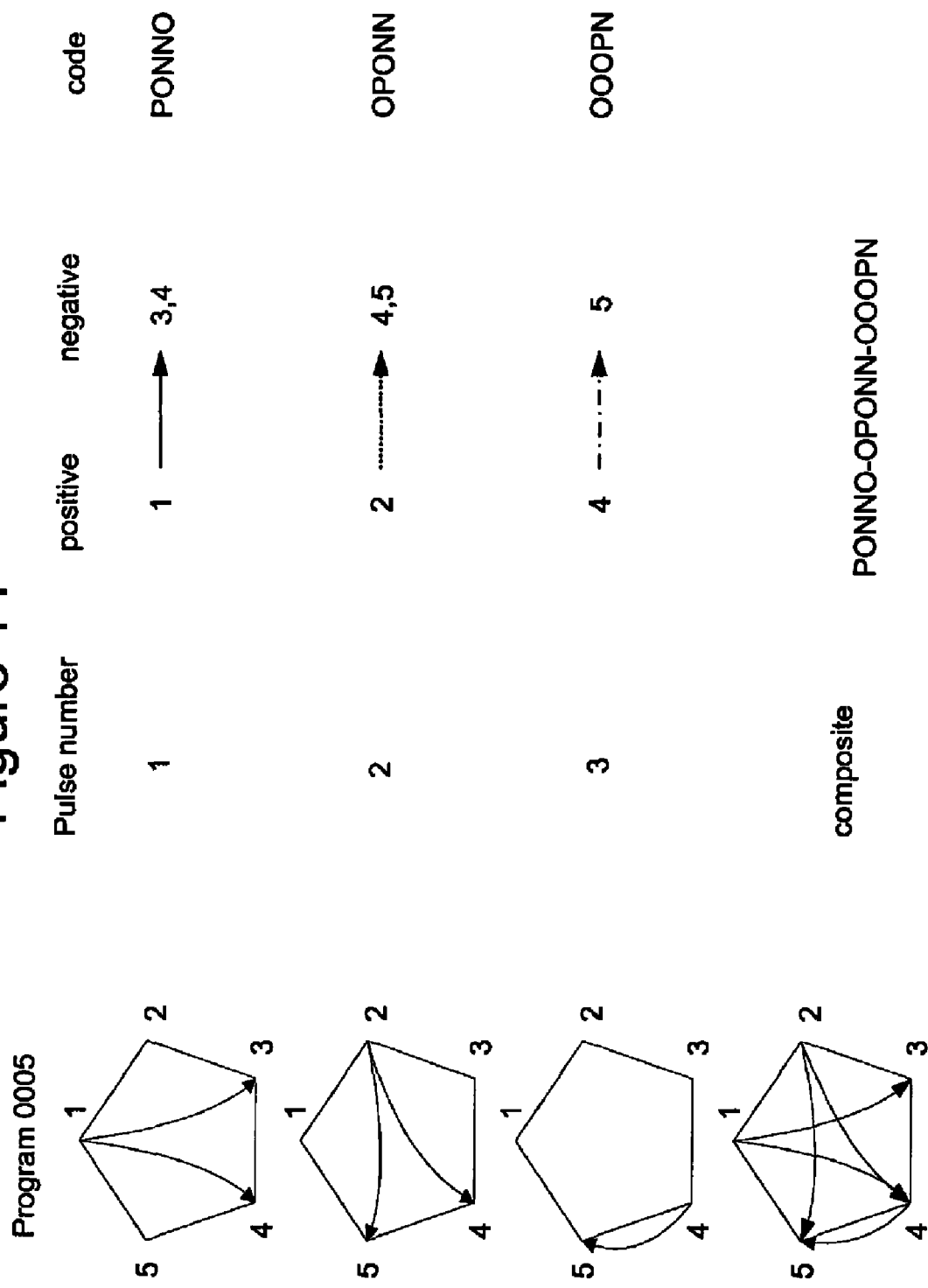
FIG. 14 shows an example of a programmed electrode pulse pattern, labeled Program 0005, for the EKD.
Figure 15:
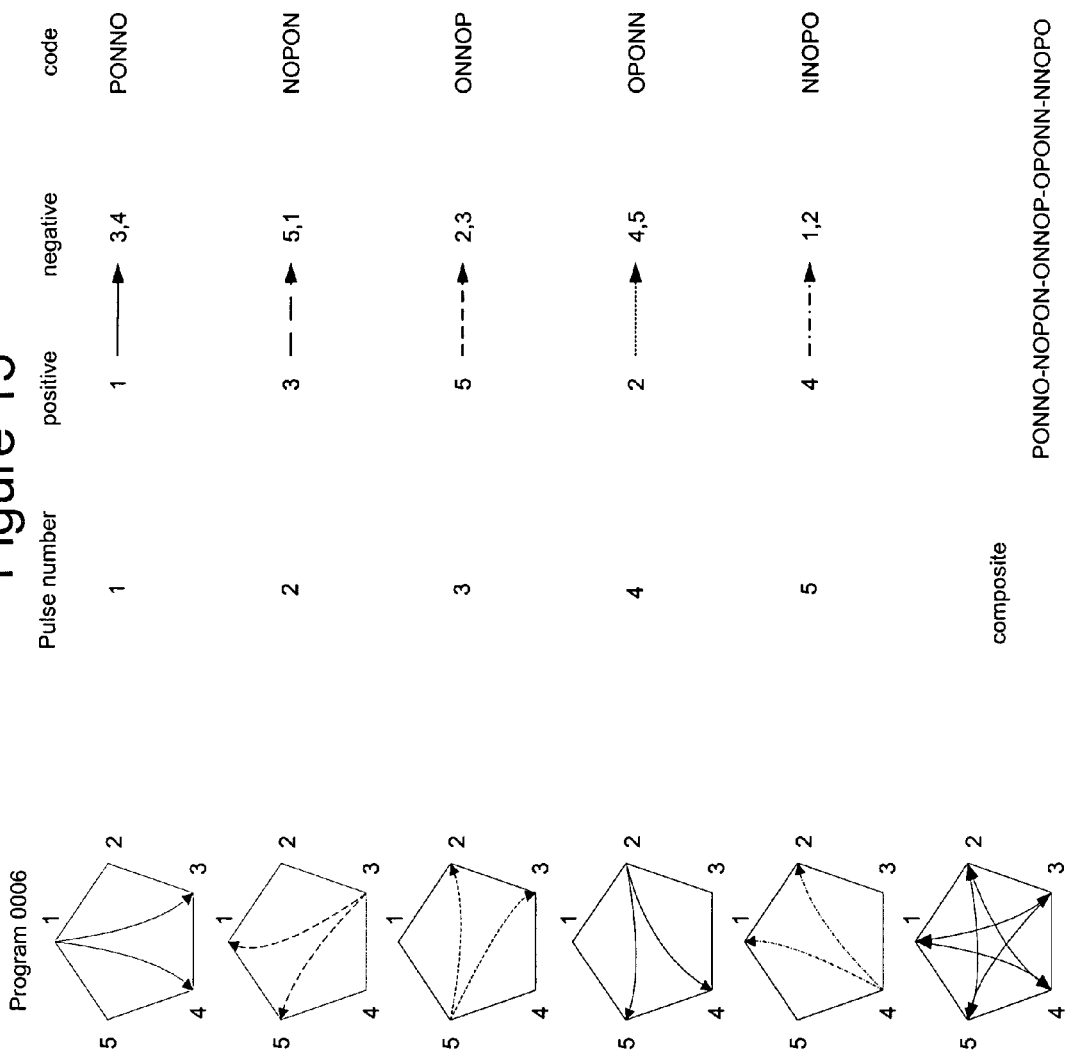
FIG. 15 shows an example of a programmed electrode pulse pattern, labeled Program 0006, for the EKD.
Figure 16:
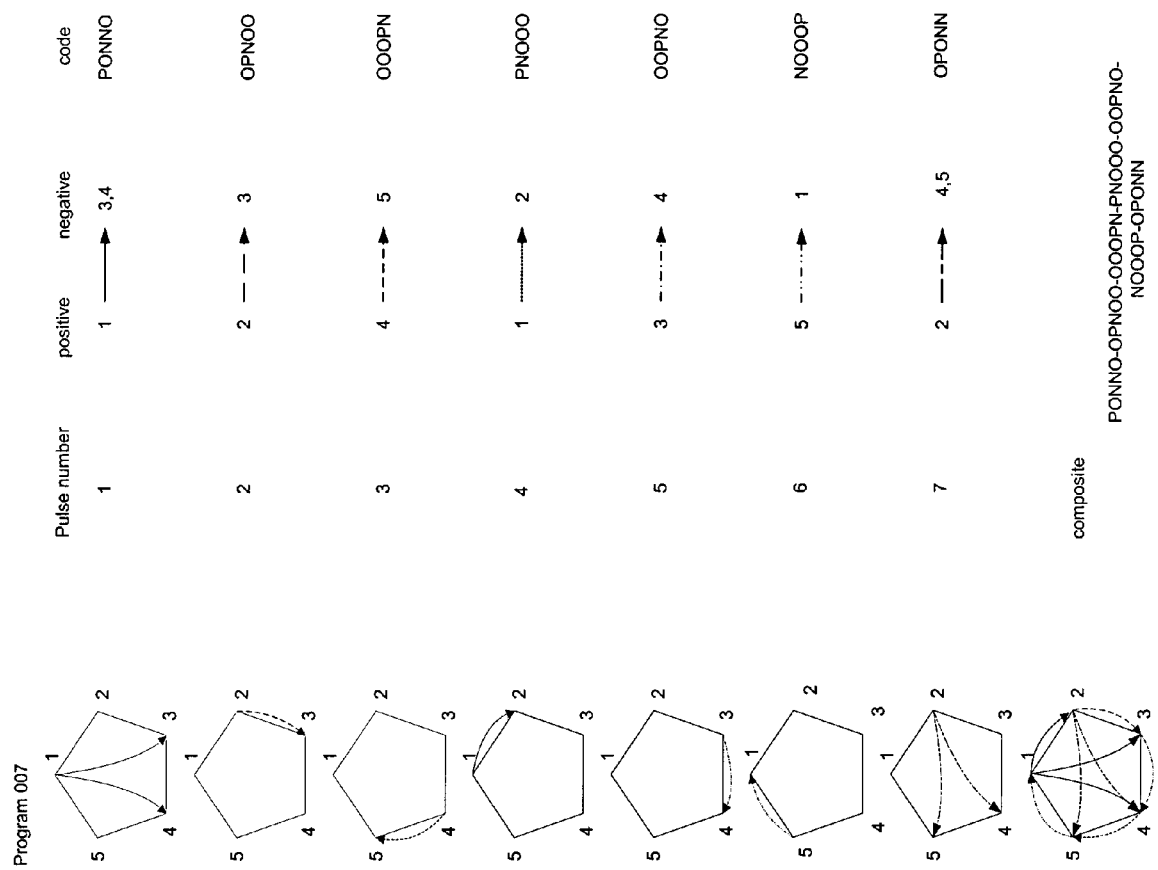
FIG. 16 shows an example of a programmed electrode pulse pattern, labeled Program 0007, for the EKD.
Figure 17:
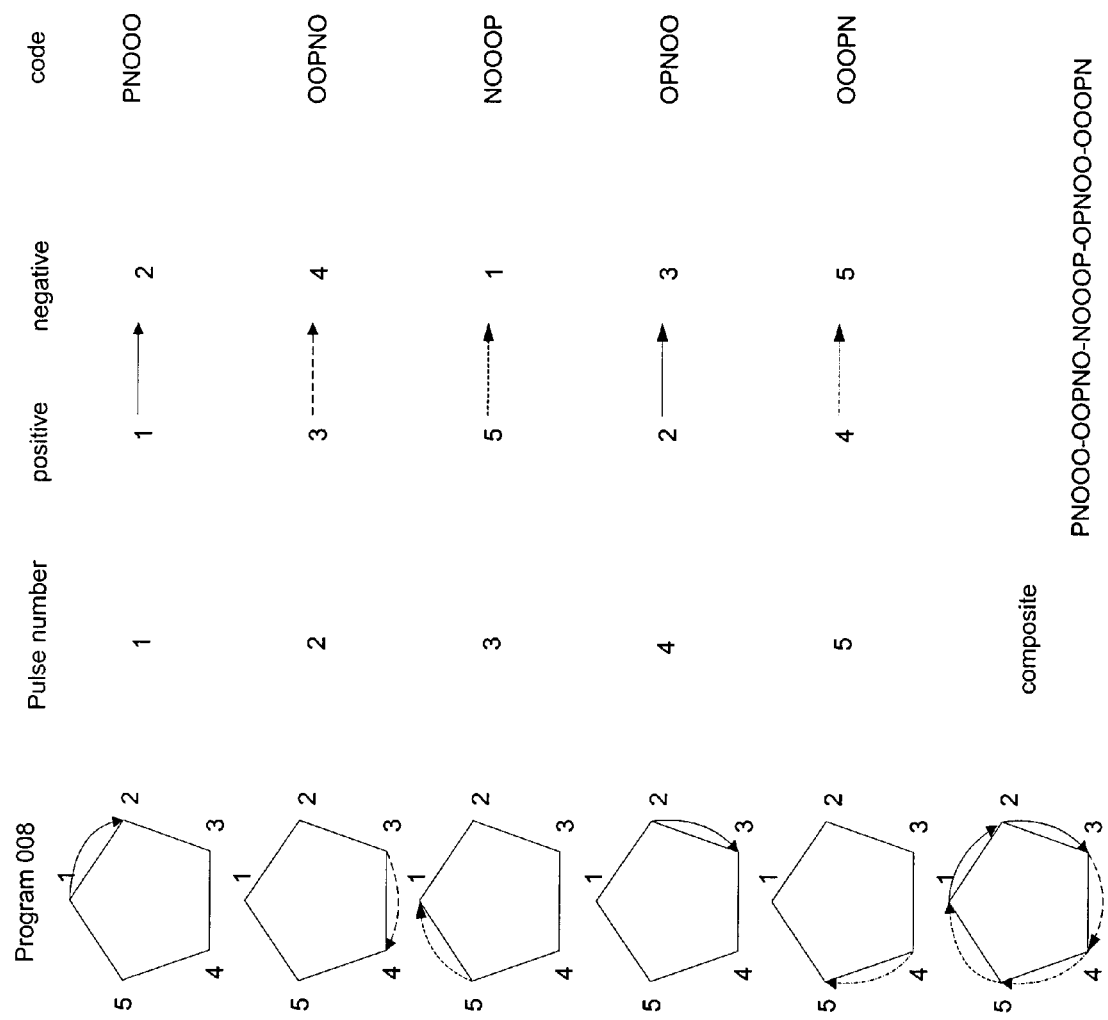
FIG. 17 shows an example of a programmed electrode pulse pattern, labeled Program 0008, for the EKD.
Figure 18:
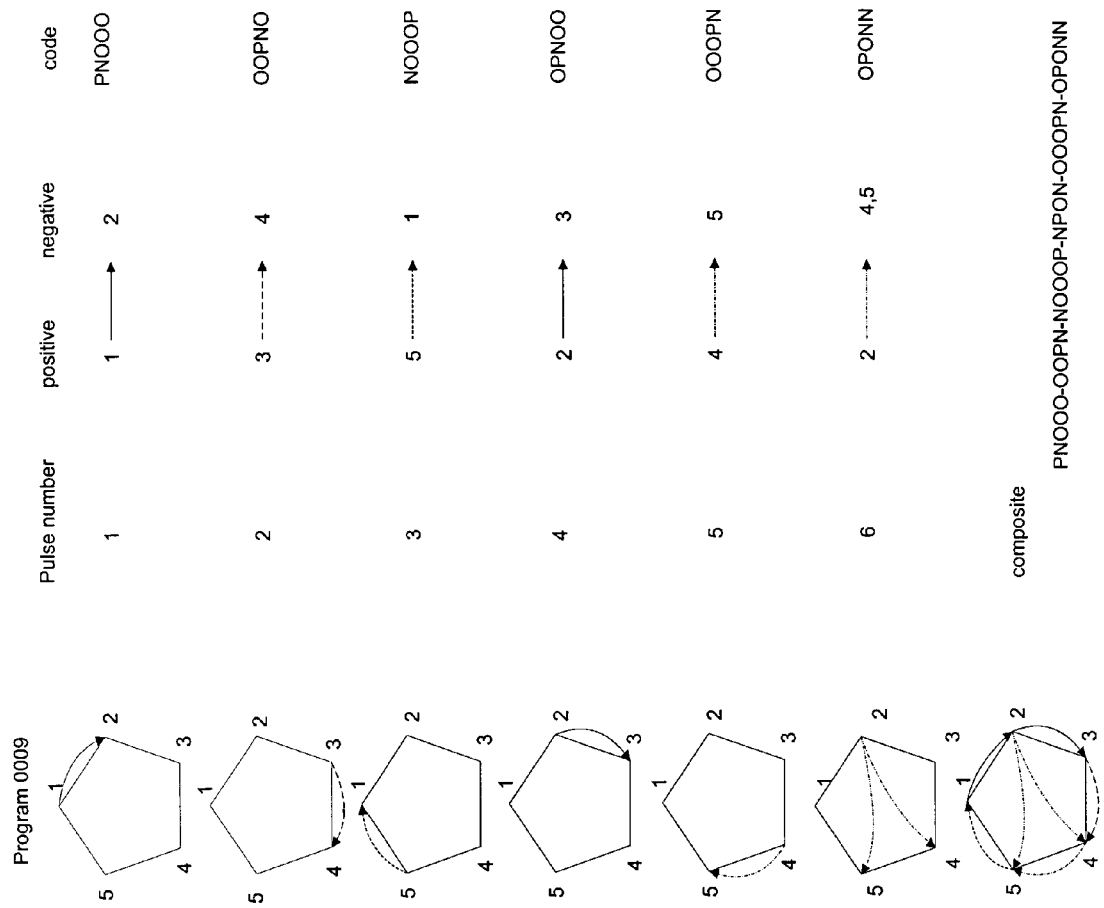
FIG. 18 shows an example of a programmed electrode pulse pattern, labeled Program 0009, for the EKD.

Because the waveforms required for electroporation are specified by software or firmware, the EKD differs from other electroporation devices, which rely on hardware specifications. For example, as shown in FIG. 8, in a programmed sequence designated Program 0000, the number of pulses is 5. For pulse 1, current flow is from electrode 1 to electrodes 3 and 4. Electrode 1 is therefore positive and electrodes 3 and 4 are negative. Electrodes 2 and 5 are electrically isolated from electrodes 1, 3 and 4. Isolation voltage is at least 200V. The entire sequence is depicted in which electrodes 1 through 5 become the positive electrode successively, with two negatively charge electrodes at opposite vertices of the pentagonal array. The code for the electrode configuration is P=positive, O=off and N=negative. The composite diagram is the sum of all pulses, and the direction of current flow, using the conventional physics notation.

The typical current pulses produced in Program 0000 are shown in FIG. 9A. FIG. 9B shows the waveform of each current pulse. The waveform parameters are:

Period ($t_p$): 1000 ms±250 µs.
Rise time ($t_r$): 20 µs maximum.
Settling time ($t_s$): 20 µs maximum.
Pulse width ($t_w$): 52 ms±100 µs.
Fall time ($t_f$): 20 µs maximum.
Nominal current ($I_n$):$I_n \epsilon \{0.1$ A, 0.2 A, 0.3 A ... 1.5 A$\} \pm 10\%$ of $I_n$ during $t_h$ and with $R_l \leq 100\Omega$. $R_l$ is the load resistance between anyone of the 5 electrode sets shown in FIG. 8.

Only the current waveform is specified in FIG. 9B. The shape of the voltage waveform depends on the impedance seen by the electrodes while the current pulse is firing (during $t_h$). The voltage waveform is not specified during $t_h$ since the impedance is unknown during this period. The voltage across any electrode set during $t_l$ is 0 V.

The EKD is programmable to utilize a variety of electrode pulse patterns. Examples of these pulse patterns are illustrated in FIGS. 10-18. Each pattern may test hypotheses related to providing optimum transgene expression by varying the volume of tissue electroporated, the potential damage associated with current flow in opposite directions through the same tissue volume, and the total current per tissue volume.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls which, under normal circumstances, maintain a resting transmembrane potential of 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula E=V/d, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation, not electric field per se. The activation of the EKD's current waveform generator will distribute a constant-current electrical pulse to the plurality of needle electrodes such that a decentralized electroporation event occurs in an area where no congruent electroporation overlap points develop. The permeability of the cells in the area of decentralized electroporation increases and the macromolecule are delivered into the cell of the subject without overheating and damaging the cell or tissue.

The present invention pertains to an electroporation device for introducing macromolecules into one or more cells of an animal or plant. The electroporation device comprises the EKD and an electrode assembly. The electroporation device may also comprise a replaceable, or exchangeable, electrode disk having a plurality of needle electrodes, a central channel or port, and an optional removable guide disk. Together the replaceable, or exchangeable, electrode disk and guide disk form a needle electrode assembly that can be mounted on a handle of an electroporation device. The handle contains an electrical connector from the needle electrode assembly to a constant-current pulse generator subsystem or the EKD. The handle is non-conductive and designed to provide a user an easy means for implanting the needle electrode assembly into a selected tissue. The utilization of disposable needle assembly and snap-on mounts on the handle allows a user to quickly attach and detach the needle electrode assembly. The guide disk provides a means for grasping the electrode assembly without contaminating the sterile needles. The power source of the electroporation device, in particular the EKD, can utilize battery packs for use in the field where access and use of a plug in power source is dangerous or inconvenient.

It should also be understood that numerous changes and modifications of the EKD and electrode assembly itself may be made therein without departing from the spirit and the scope of the invention as defined in the claims. For example, in another embodiment, the invention provides a method for delivery of a macromolecule to a cells that make up the blood vessel walls or simply cells in culture. With modifications, the needle electrode array could be converted into a catheter electrode array that is connected to the same EKD described herein. The catheter could be placed inside a blood vessel and macromolecules could then be delivered directly into the vessel wall utilizing a constant-current protocols described herein, which would not overheat or destroy the wall of the blood vessel. The constant-current pulse would be generated by the EKD. This method will not cause cell death due to heating. Such an apparatus and method would be an excellent mechanism for direct and more regulated delivery of macromolecules into the blood stream.

The concept can be extended to any number of electrodes, such as a three-electrode array. The distance L is chosen so that the energy intensity at point B is one third of that at point A. After three pulses, (1 to 2, 2 to 3 and 3 to 1), point B has received a cumulative dose equal to that of point A. As the number of electrodes in the array is increased, the distance L necessary to yield a uniform energy distribution becomes proportionately longer. L=k×n where n is the number of electrodes, and k is a proportionality constant. Thus, by selecting a greater number of electrodes a greater volume of tissue can be encompassed. The optimal number of electrodes chosen may depend on the volume of the material to be transfected and how far it is dispersed between injection and electroporation.

A syringe with a specially designed macromolecule injection cartridge can also be used to deliver a single dose concentration of pre-sterilized macromolecules into a body or plant. This macromolecule injection cartridge may be a plastic container portion that contains the single dose concentration of pre-sterilized macromolecules and a pre-sterilized hollow sharp needle extending from the plastic container portion that will convey fluids from within the container out through the tip of the hollow needle when the needle is inserted into the body or plant. The central injection channel of the electrode disk ensures that the pre-sterilized macromolecules and needle are not contaminated during the injection process.

Example 1

Operation of the Electro-Kinetic Device ("EKD")

Figure 19:
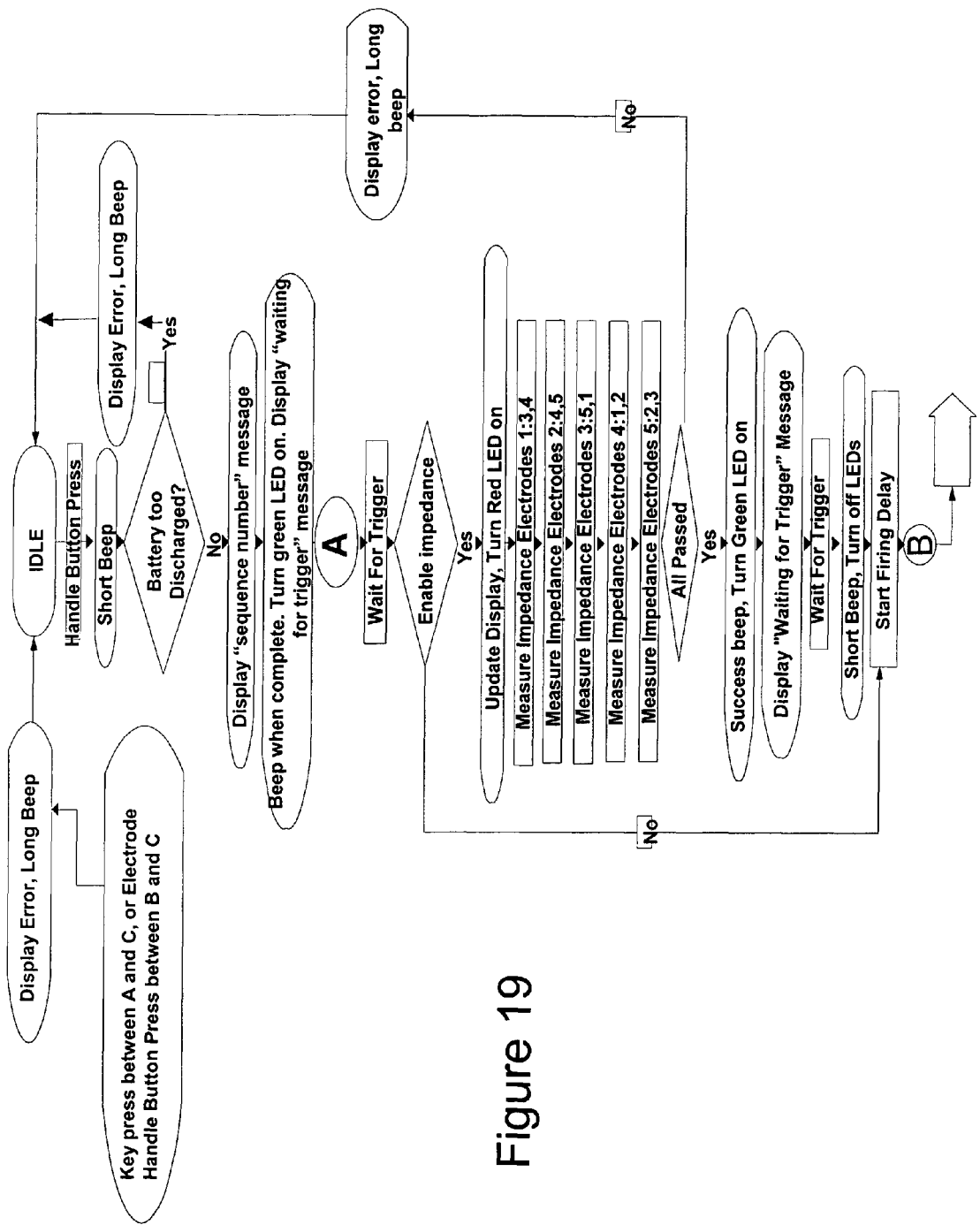
FIG. 19 shows a diagram of the first half of a sample delivery operation sequence for the EKD.
Figure 20:
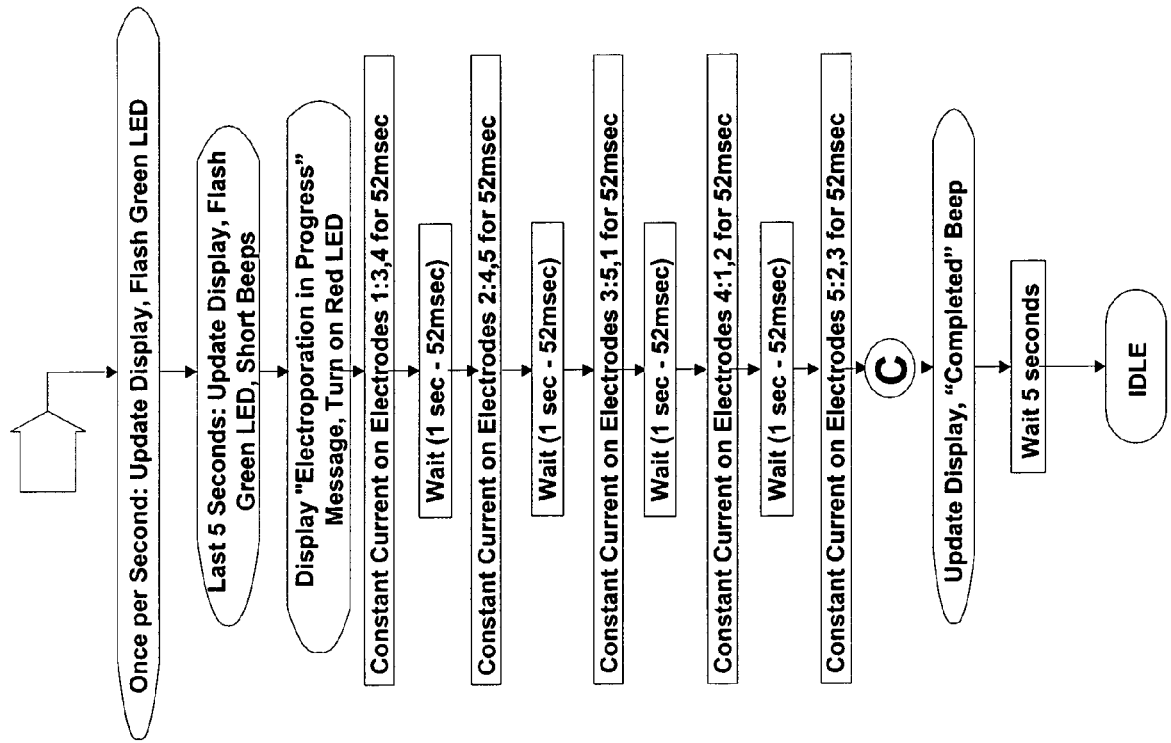
FIG. 20 shows a diagram of the second half of a sample delivery operation sequence for the EKD.

The operation of the Controller is shown in FIGS. 19 and 20, which illustrate a preferred operation sequence of the EKD. In a preferred embodiment, an information display panel LCD displays each step of the sequence to promote user-friendly operation. Prior to operating the EKD, the electrode assembly is firmly inserted into the target tissue.

First, the power is turned on and the EKD is booted up. The firmware remains in the idle state until input is received from the user. To start an electroporation sequence, a password is entered to obtain an introductory prompt on the LCD. At this point, the handle assembly activator switch is pressed. The user then enters a number, preferably an animal ID number, which is logged with the data of every pulse stored for later download. The number is preferably entered using a numeric keypad. The user is then prompted, via a "beep" from the buzzer, to press the activation switch to continue the electroporation sequence. After the activation switch is pressed, the firmware establishes whether or not the impedance tester is enabled. If the impedance tester is enabled, the software immediately performs a series of impedance measurements. The firmware tests the impedance between electrodes with a low DC voltage. These measurements are performed as quickly as possible to get sufficiently accurate readings. During the impedance testing, a red LED on the handle assembly is lit. If any of the 5 impedance measurements fail, a long error "beep" will sound, the handle LED will stay red, the LCD will display the error, and the firmware will return to the idle state.

If all 5 measurements pass, a short "beep" is emitted, a green LED on the handle assembly is lit, and the display prompts the user to press the activation switch to continue. The firmware waits for the handle activation switch to be pushed again to continue the sequence. If any key on the keypad is pressed at this time, a long error "beep" will be sounded and the unit will return to the idle state.

Typically, the plasmid is injected into the muscle at this point in the sequence. When plasmid injection is complete, the user pushes the activation switch to continue the electroporation sequence. A short "beep" emits, and the firmware counts down using a programmed firing delay to the actual electrode-firing sequence. During the firing delay, the green LED on the handle assembly flashes once per second. If any key on the keypad is pressed at this time, a long error "beep" emits and the unit returns to the idle state. For the last 5 seconds before the electroporation, the buzzer makes an intermediate-length "beep" once per second.

At the end of the firing delay, the firmware implements the firing sequence as proscribed by the pulsing program selected. The red LED on the handle assembly lights up every second for roughly 500 ms during the 5-second period of electroporation. When the electroporation sequence is completed successfully, the EKD returns to the idle state. If the total current delivered was less than that specified by the firmware, an error message is displayed. The fraction of current delivered, compared to that specified, is given as the percentage complete.

Example 2

Data Acquisition and Storage

The EKD software or firmware enables real time data acquisition and storage in non-volatile memory. FIG. 21 illustrates a first portion of data that may be collected during the electroporation process. The first section of the file header contains the file name and the animal number. The columnar data describes the pulse in sequence, the wait time before pulsing, the pulse width, and the pulse current for each of the five electrodes. FIG. 22 illustrates a second portion of data, which identifies the configuration of each electrode during a given pulse sequence. Reading vertically for the first pulse, electrode 1 is positive, 2 is off, 3 is negative, 4 is negative, and 5 is off. The electrode configurations for pulses 2, 3, 4, and 5 constitute the remainder of the data columns. FIG. 23 illustrates a formatted version of a third portion of raw data for the same electroporation, which consists of 10 time points, about 20 ms apart, for the five electrodes. Reading vertically for the first pulse, column 1 records the voltage and column 2 the current. The voltage-current data for pulses 2, 3, 4, and 5 are found in columns 3 and 4, 5 and 6, 7 and 8, and 9 and 10, respectively.

Example 3

Plasmid Design, Delivery Methods, and Experimental Animals

Plasmid construction. The plasmid pSP-SEAP (5019 bp) is a muscle specific expression plasmid for secreted embryonic alkaline phosphatase ("SEAP"). The promoter is SPc5-12, a strong, muscle specific, synthetic promoter (Li et al., 1999), and the 3' ends of SEAP transcripts are defined by the SV40 late poly(A) signal. The plasmid was constructed by inserting a 394 bp Acc65I-HindIII fragment, containing the 334 bp SPc5-12 promoter sequence, between the Acc65I and HindIII sites of pSEAP-2 Basic Vector (Clontech Laboratories, Inc., Palo Alto, Calif.).

Electroporation conditions. Square wave pulses were used in all experiments. Electroporation conditions are stated individually for each experiment. In all cases, constant current was used at 0.4 to 1.0 Amps, with 3 or 5 pulses, for 52 milliseconds/pulse, and with one second between pulses. The EKD electroporation device contained a circular array (1 cm diameter) of five equally spaced 21-gauge solid stainless steel needle electrodes, mounted on a non-conductive material. The electrode disk had a central channel through which the injection needle could be inserted into the muscle, such that the plasmid was delivered within the area that was delineated by the surrounding five electrodes. All electrodes were 2 cm in length and were completely inserted through the skin into the muscle during all treatments. In all but one experiment, the EKD (ADViSYS) was used. In the last experiment, a different model of electroporation device (ADViSYS Enducer Model BB) was used for comparison purposes.

Intramuscular injection of plasmid DNA in pigs. Young hybrid pigs of mixed gender, three to six weeks of age, with weights between 15-40 kg, were used in the SEAP studies (n=6 to 7/group/experiment). Animals were housed in groups in pens with ad libitum access to a 24% protein diet (Producers Cooperative Association, Bryan, Tex.) and water. Endotoxin-free plasmid preparations were diluted in sterile water and formulated at 1% weight/weight with poly-L-glutamate. On Day 0 of the experiment, the animals were manually restrained and the SEAP plasmid solution was directly injected through the intact skin into the semimembranosus muscle using a 21-gauge needle. All major surface blood vessels were avoided when finding an appropriate injection site. At a pre-determined time interval after plasmid injection, electroporation was applied through the 5-electrode array.

Blood collection. On days 0, 3, 7, 10, and 14 of each experiment, the animals were weighed and blood was collected by jugular vein puncture into MICROTAINER serum separator tubes. Blood was allowed to clot for 10 to 15 min. at room temperature and was subsequently centrifuged at 3000×g for 10 min. The serum was stored at −80° C. until further analysis.

Secreted embryonic alkaline phosphatase assay. Serum samples were thawed and 50 μL was assayed for SEAP activity using the Phospha-Light™ Chemiluminescent Reporter Assay Kit (Applied Biosystems, Bedford, Mass.), per manufacturer instructions. The lower limit of the detection of the assay was 3 pg/mL. More concentrated serum samples were diluted 1:10 in mouse serum before assaying for SEAP activity. All samples were read using a LUMIstar Galaxy™ luminometer (BMG Labtechnologies, Offenburg, Germany).

Statistics. Data were analyzed using Microsoft Excel™ Statistics package. Values shown in the figures are the mean±SEM. Specific values were obtained by comparison using t-test or one-way ANOVA. A value of p<0.05 was set as the level of statistical significance.

Example 4

Effects of Plasmid Dose

Figure 24:
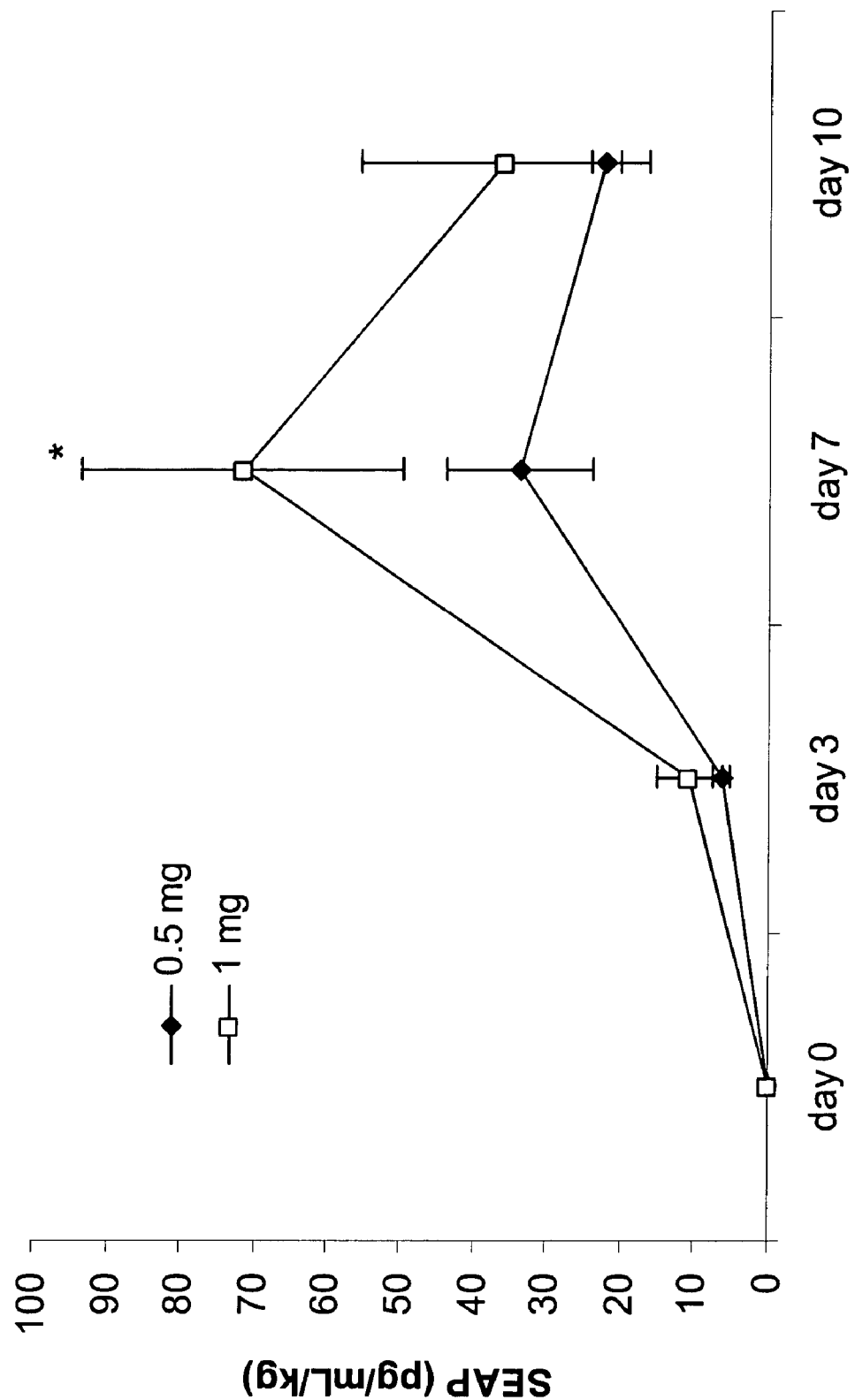
FIG. 24 shows the expression levels of SEAP in animals which were injected with different amounts of the plasmid pSP-SEAP and electroporated with the EKD in pulse pattern Program 0000.

Animals were injected with either 0.5 mg or 1 mg SEAP expressing plasmid in a total volume of 2 mL. The intensity of the electric field was 0.5 A using Program 0000 (FIG. 8). The lag time between plasmid injection and electroporation was 80 seconds. As illustrated in FIG. 24, the expression of SEAP was dependent on the amount of plasmid administered. At Day 7, post-injection SEAP expression in animals treated with 1 mg plasmid was 2.1 fold that of animal treated with 0.5 mg plasmid (71.6±22 versus 33.7±10 pg/mL/kg, * P<0.09, due to high inter-animal variability at higher plasmid doses). In all subsequent experiments, a total 0.5 mg plasmid dose was used.

Example 5

Effects of Plasmid Volume

Figure 25:
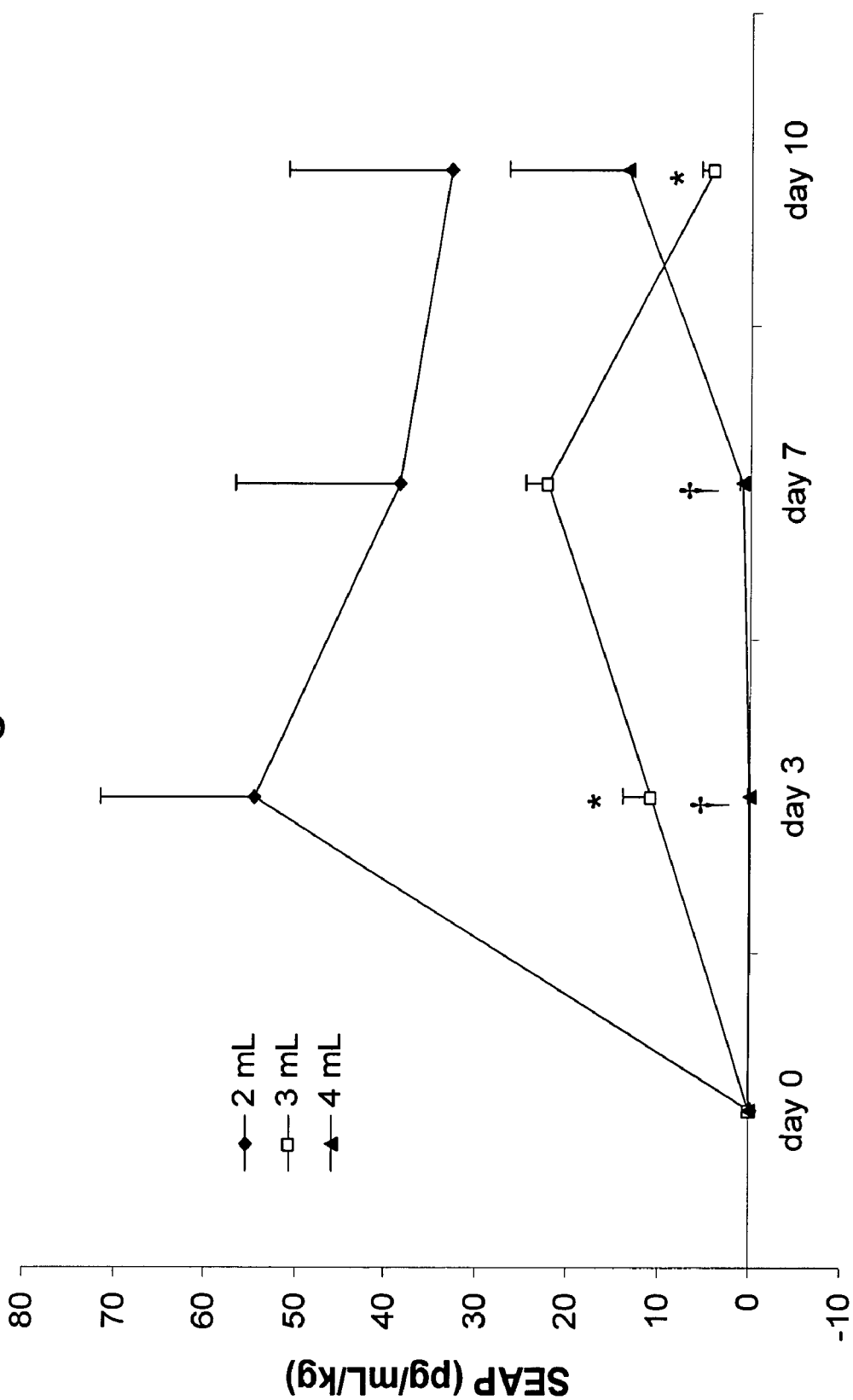
FIG. 25 shows the expression levels of SEAP in animals which were injected with the same amount of plasmid pSP-SEAP in different volumes and electroporated with the EKD in pulse pattern Program 0000.

Animals were injected with 0.5 mg SEAP expressing plasmid in a total volume of 2, 3 or 4 mL water. The intensity of the electric field was 0.5 A using Program 0000 (FIG. 8). The lag time in between plasmid injection and electroporation was 80 seconds. As shown in FIG. 25, SEAP expression was dependent on the plasmid volume. At Day 3, SEAP expression was significantly higher in animals administered the plasmid in a 2 mL injection volume: 54±17 pg/mL/kg, * P<0.02 versus 11±3 pg/mL/kg in the 3 mL-treated group, and 0.13±0.3 pg/mL/kg in the 4 mL-treated group, † P<0.03; at Day 7, 38.5±18 pg/mL/kg, † P<0.05 versus 1±0.3 pg/mL/kg in the 4 mL-treated group; and at Day 10 * P<0.04 versus 3 mL-treated group.

Example 6

Effects of Electric Field Intensity

Figure 26:
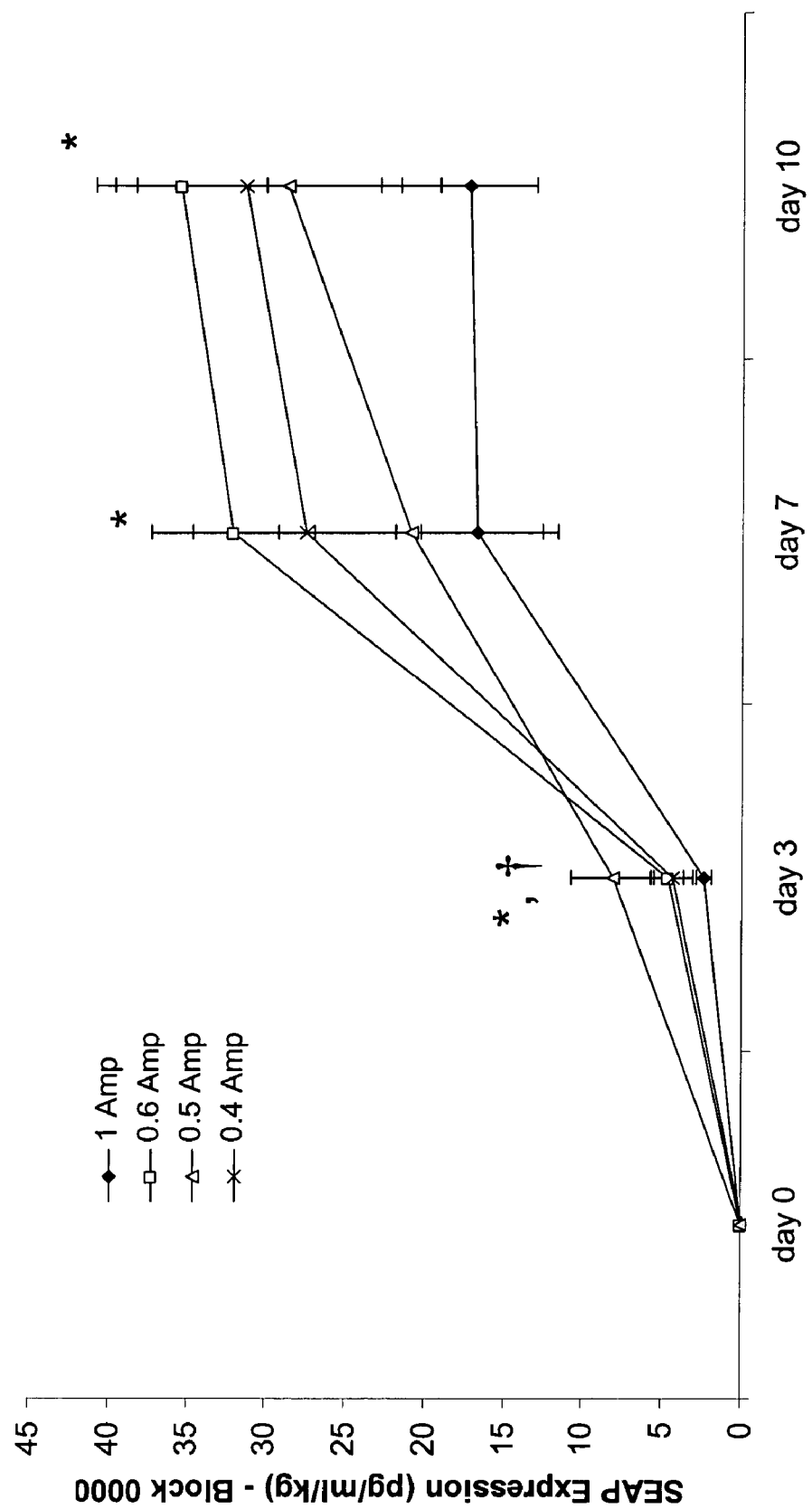
FIG. 26 shows the expression levels of SEAP in animals which were injected with the same amount of plasmid pSP-SEAP and electroporated with the EKD in pulse pattern Program 0000 at different electric field intensities.

Electric field intensity correlates with pulse pattern for optimum plasmid uptake and transgene expression. In a first experiment, all animals were injected with 0.5 mg SEAP expressing plasmid in a total volume of 2 mL. The lag time between the injection and electroporation was 80 seconds. Using the EKD Program 0000 (FIG. 8) pulse pattern, the intensity of the electric field was decreased from the 1 Amp positive controls to 0.6 Amp, while expression is increased, as shown in FIG. 26. The 1 Amp condition was chosen because of the substantial body of literature with data from constant voltage electroporation devices which suggest that this electric field intensity would yield the best expression level (Mir et al., 1998). As stated, in this case the best results were obtained using an electric field intensity of 0.6 Amps. At Day 3—* P<0.04 for 0.6 Amp and † P<0.03 for 0.5 Amp; at Day 7—* P<0.03 for 0.6 Amp; and at Day 10—* P<0.01 for 0.6 Amp.

Figure 27:
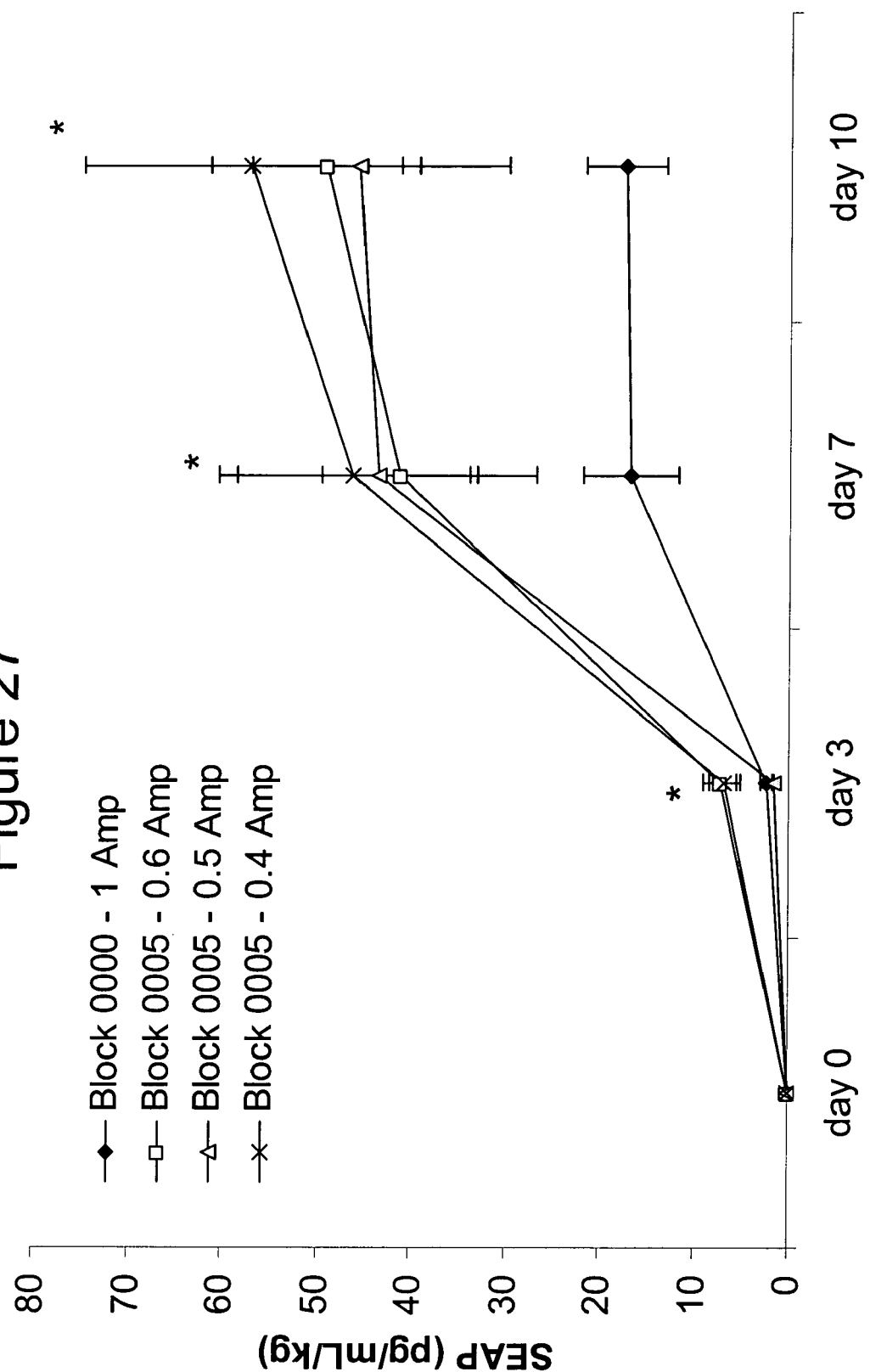
FIG. 27 shows the expression levels of SEAP in animals which were injected with the same amount of plasmid pSP-SEAP and electroporated with the EKD in different pulse patterns and at different electric field intensities.

Further comparison was performed between electric field intensities, using a different pulse pattern model. Electric field intensities of 0.4, 0.5 and 0.6 Amp, using the Program 0005 pulse pattern (FIG. 14—three pulses, no reverse of electric field), were compared to 1 Amp using the Program 0000 pulse pattern (FIG. 8—five pulses, complete reverse of electric field), as a positive control reference. All animals were injected with 0.5 mg SEAP expressing plasmid in a total volume of 2 mL. The lag time between plasmid injection and electroporation was 80 seconds. Using this pulse pattern, as shown in FIG. 27, the best expression levels were obtained using an electric field of only 0.4 Amp: at Day 3—* P<0.02 for 0.4 Amp; Day 7—*P<0.03 for 0.4 Amp; and Day 10—*P<0.03 for 0.4 Amp. At all time points tested, the group treated at 0.5 Amp had a trend towards increased SEAP values (P=0.06-0.07).

Example 7

Effects of Lag Time

Figure 28:
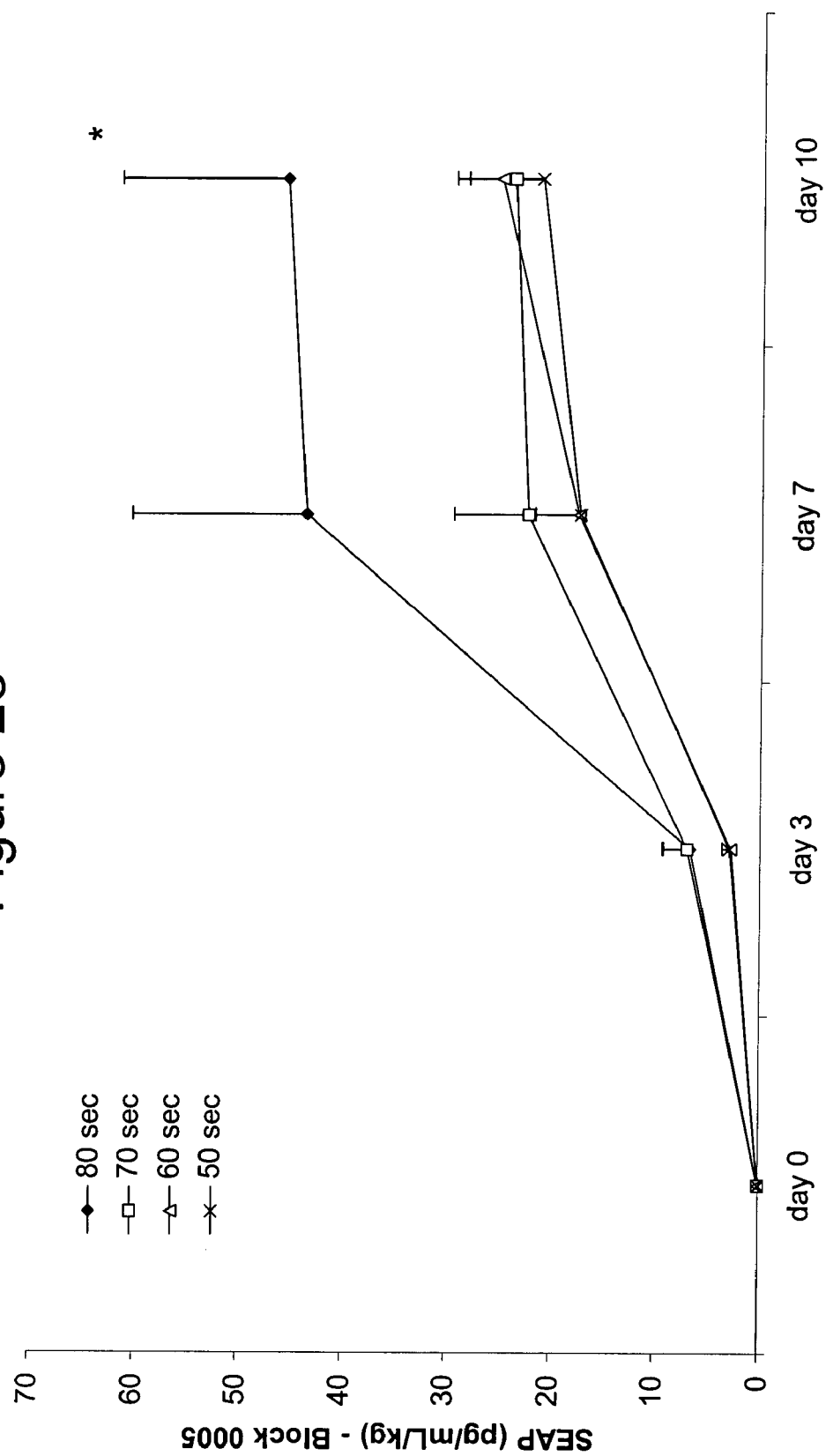
FIG. 28 shows the expression levels of SEAP in animals which were injected with the same amount of plasmid pSP-SEAP and electroporated with the EKD after different lag times between plasmid injection and the first pulse of pulse pattern Program 0000.
Figure 29:
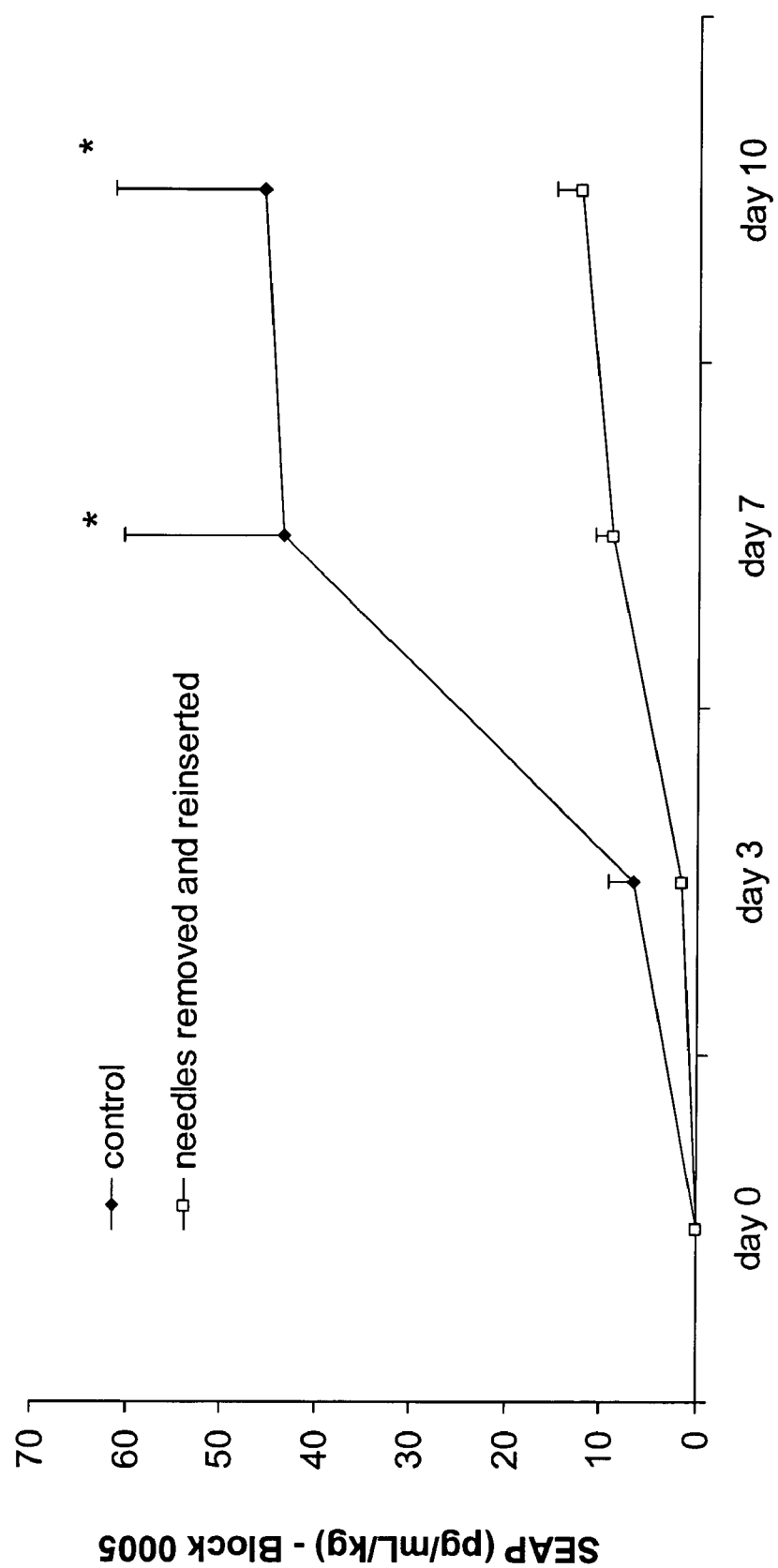
FIG. 29 shows the expression levels of SEAP in animals which were injected with the same amount of plasmid pSP-SEAP and electroporated either contemporaneously or after electrode removal and repositioning in the muscle.

Previous experiments utilized a 2 minute lag time between plasmid injection and electroporation (Draghia-Akli et al., 1999; Mir et al., 1999). To facilitate large-scale applications of the technology, it is important to consider shortening the lag time as much as possible. However, as shown in FIG. 28, the lag time between plasmid injection and electroporation should be no less than 80 seconds. In this experiment, all animals were injected with 0.5 mg SEAP expressing plasmid in a total volume of 2 mL. The intensity of the electric field was 0.5 A. SEAP expression levels decreased when the lag time was reduced from 80 to 70, 60 or 50 seconds. There was a clear reduction in SEAP expression levels at lag times less than 80 seconds: Day 10—* P<0.05 between the group electroporated at 50 seconds and the group that received the electroporation at 80 seconds post-injection. Although not wanting to be bound by theory, this lag time may be necessary to allow to the injected plasmid to distribute in the muscle and bind to the membrane surface before it is electrically and reversibly restructured.

Example 8

Delineation of Injection Area

Commercially available electroporation devices and needle arrays do not permit injection and electroporation in one combined operation. With these instruments, the procedure required that the injection needle be inserted into the target muscle for plasmid delivery, then removed from the muscle. The electrodes were then inserted into the muscle in the proximity of the injected area, usually based on a skin tattoo. However, the underlying muscle may move or contract, so the injection site may not be completely circumscribed by the needle electrodes.

In this experiment, all animals were injected with 0.5 mg SEAP expressing plasmid in a total volume of 2 mL. The intensity of the electric field was 0.5 A. The lag time between the injection and electroporation was 80 seconds. One group of animals had the needles inserted into the target muscle, and held in place for the entire procedure. In a second group the needles were removed immediately after the plasmid injection, reinserted after 15 seconds into the same injection site visualize on the skin, and the 80 seconds count down started. SEAP levels were 43.5±16.8 pg/mL/kg in Group A versus 9±1.7 pg/mL/kg at Day 7—* P<0.02; and 45.6±16 pg/mL/kg versus 12±2.5 pg/mL/kg at Day 10—* P<0.02. As shown in FIG. 28, the non-specificity of the electroporation site reduced plasmid expression by up to 75%. This finding emphasizes the importance of precisely and accurately electroporating the injection site for greater gene expression.

Example 9

Comparative Study

Escalating pSP-SEAP doses from 0 to 10 mg were administered in accordance with the previous examples. Plasmid injection was followed by electroporation using a different electroporation device (ADViSYS Enducer Model BB, U.S. patent application Ser. No. 10/360,768). As shown in FIG. 30, expression level was dose dependent. Nevertheless, at Day 7 post-injection, SEAP levels averaged 7±2.2 pg/mL/kg, while experiments using the EKD showed SEAP expression at the corresponding time point averaging 33.7±10 pg/mL/kg, a 4 fold increase. Although not wanting to be bound by theory, this increase in expression may result from the enabling step, which allows the operator to be sure that all needles are in the same muscle; the display, which allows for real time control of the procedure; the software, which allows for visualization of each pulse; and subsequent adjustment of parameters if the first electroporation procedure fails.

What is claimed is:

1. An electroporation device comprising:
    a support structure that includes a sterile injection channel adapted to receive a syringe needle;
    an electrode assembly having a plurality of needle electrodes for penetrating a selected tissue and delivering an electrical pulse, wherein the needle electrodes are mounted in an array around the sterile injection channel of the support structure;
    a current waveform generator in electrical communication with the plurality of needle electrodes, the waveform generator being capable of generating the electrical pulse;
    a power source in electrical communication with the current waveform generator;
    a controller in communication with the current waveform generator and the power source; and
    a waveform logger in communication with the controller;
    wherein the controller is capable of managing the electroporation device to expose tissue adjacent to the needle electrodes to a substantially constant current independent of any resistance change in the selected tissue during the electrical pulse, the controller is capable of sampling and monitoring the electroporation voltage and current waveforms, and the waveform logger is capable of recording the electroporation voltage and current waveforms.

2. The device of claim 1, further comprising an impedance tester in electrical communication with the plurality of needle electrodes.

3. The device of claim 1, further comprising an input device for inputting commands into the controller.

4. The device of claim 3, wherein the input device is a keypad.

5. The device of claim 1, further comprising a status-reporting device for reporting status information during the electroporation procedure.

6. The device of claim 5, wherein the status-reporting device is an information display panel, an audible notification, a light-emitting diode ("LED"), or a combination thereof.

7. The device of claim 1, further comprising a communications port in communication with the controller.

8. The device of claim 7, wherein the communications port is an optical serial communications port.

9. The device of claim 7, wherein the communications port is an infrared port.

10. The device of claim 1, further comprising memory in communication with the controller.

11. The device of claim 10, wherein the memory is non-volatile.

12. The device of claim 1, wherein the power source is a battery.

13. The device of claim 1, wherein the electrode assembly further comprises a handle to which the support structure is connected to, and further wherein the sterile injection channel extends through the handle.

14. The device of claim 13, wherein the electrode assembly further comprises an activation switch mounted on the handle and in communication with the controller.

15. The device of claim 1, wherein the array is a circular array.

16. The device of claim 15, wherein the circular array is about 1.0 cm in diameter.

17. A method for electroporating cells of a selected tissue to facilitate the introduction of macromolecules, comprising:
    programming an electrical pulse pattern into a controller of an electroporation device, wherein the electroporation device comprises:
        an electrode assembly having a plurality of needle electrodes for penetrating a selected tissue and delivering an electrical pulse, wherein the needle electrodes are mounted in an array around a sterile injection channel of a support structure;
        a current waveform generator in electrical communication with the plurality of needle electrodes, the waveform generator being capable of generating the electrical pulse;
        a power source in electrical communication with the current waveform generator;
        a controller in communication with the current waveform generator and the power source; and
        a waveform logger in communication with the controller;
    wherein the controller is capable of managing the electroporation device to expose the selected tissue to a substantially constant current independent of any resistance change in the selected tissue during the electrical pulse, the controller is capable of sampling and monitoring the electroporation voltage and current waveforms, and the waveform logger is capable of recording the electroporation voltage and current waveforms;
    inserting the plurality of needle electrodes of the electrode assembly into the selected tissue;

measuring the resistance of the plurality of needle electrodes to determine if a circuit can safely be established through the selected tissue;

injecting a solution of the macromolecules into the selected tissue by passing a syringe needle through the sterile injection channel;

generating a pulse of electrical energy from the waveform generator in accordance with the programmed electrical pulse pattern; and applying the pulse of electrical energy to the plurality of needle electrodes in accordance with the programmed electrical pulse pattern for a time and under conditions effective to expose the selected tissue to a substantially constant electrical current.

18. The method of claim 17, further comprising electronically recording data related to the electroporation through a waveform logger in communication with the controller.

19. An electroporation device comprising:

an electrode assembly having a support structure including a sterile injection channel, and an electrode disk comprising a plurality of needle electrodes for penetrating a selected tissue and delivering an electrical pulse, wherein the needle electrodes are mounted in an array around the sterile injection channel and the sterile injection channel is adapted to receive a syringe needle;

a current waveform generator in electrical communication with the plurality of needle electrodes, the waveform generator being capable of generating the electrical pulse;

a power source in electrical communication with the current waveform generator;

a controller in communication with the current waveform generator and the power source, wherein the controller is comprised of firmware;

and a waveform logger in communication with the controller;

wherein the controller is capable of sampling and monitoring the electroporation voltage and current waveforms, and the waveform logger is capable of recording the electroporation voltage and current waveforms, and the firmware is capable of managing the waveforms generated by the waveform generator to expose tissue adjacent to the needle electrodes to a substantially constant current independent of any resistance change in the selected tissue during the electrical pulse.

20. The electroporation device of claim 19, wherein the electrode disk is a replaceable disk.

21. The electroporation device of claim 19, wherein the array is a circular array.

* * * * *